(12) United States Patent
Jeon et al.

(10) Patent No.: US 11,541,099 B2
(45) Date of Patent: Jan. 3, 2023

(54) FLOUNDER SURIMI HAVING ANTIOXIDANT AND ANTIHYPERTENSIVE EFFECTS AND METHOD OF PREPARING THE SAME

(71) Applicant: Jeju National University Industry-Academic Cooperation Foundation, Jeju-si (KR)

(72) Inventors: You-Jin Jeon, Jeju-si (KR); Jae-Young Oh, Jeju-si (KR)

(73) Assignee: JEJU NATIONAL UNIVERSITY INDUSTRY-ACADEMIC COOPERATION FOUNDATION, Jeju-si (KR)

( * ) Notice: Subject to any disclaimer, the term of this patent is extended or adjusted under 35 U.S.C. 154(b) by 255 days.

(21) Appl. No.: 16/609,807

(22) PCT Filed: Aug. 30, 2018

(86) PCT No.: PCT/KR2018/010028
§ 371 (c)(1),
(2) Date: Oct. 31, 2019

(87) PCT Pub. No.: WO2019/045467
PCT Pub. Date: Mar. 7, 2019

(65) Prior Publication Data
US 2020/0179481 A1    Jun. 11, 2020

(30) Foreign Application Priority Data

Aug. 31, 2017  (KR) .......... 10-2017-0111310
Sep. 1, 2017   (KR) .......... 10-2017-0111944

(51) Int. Cl.
| | |
|---|---|
| *A61K 38/17* | (2006.01) |
| *A23L 33/18* | (2016.01) |
| *A23L 17/20* | (2016.01) |
| *A23L 17/00* | (2016.01) |
| *A61K 38/08* | (2019.01) |
| *A61K 38/00* | (2006.01) |
| *C07K 7/06* | (2006.01) |
| *A61K 38/01* | (2006.01) |
| *A23L 27/40* | (2016.01) |
| *A61P 39/06* | (2006.01) |
| *A61P 9/12* | (2006.01) |
| *A61K 38/48* | (2006.01) |
| *C07K 1/12* | (2006.01) |

(52) U.S. Cl.
CPC .......... *A61K 38/1706* (2013.01); *A23L 17/20* (2016.08); *A23L 17/70* (2016.08); *A23L 27/40* (2016.08); *A23L 33/18* (2016.08); *A61K 38/08* (2013.01); *A61K 38/488* (2013.01); *A61K 38/4826* (2013.01); *A61P 9/12* (2018.01); *A61P 39/06* (2018.01); *A23V 2002/00* (2013.01); *A61K 38/00* (2013.01); *A61K 38/01* (2013.01); *C07K 1/12* (2013.01); *C07K 7/06* (2013.01)

(58) Field of Classification Search
None
See application file for complete search history.

(56) References Cited

U.S. PATENT DOCUMENTS

| | | | |
|---|---|---|---|
| 2014/0072650 A1 | 3/2014 | Kim et al. | |
| 2018/0258462 A1* | 9/2018 | Statsyuk | ............... C12N 9/104 |

FOREIGN PATENT DOCUMENTS

| | | | | |
|---|---|---|---|---|
| JP | 11023531 A | * | 1/1999 | |
| KR | 10-0600578 | | 7/2006 | |
| KR | 10-0946997 | | 3/2010 | |
| KR | 10-1404850 | | 6/2014 | |
| KR | 10-1449804 | | 10/2014 | |
| WO | WO-03085081 A2 | * | 10/2003 | .............. A61P 35/00 |

OTHER PUBLICATIONS

Chen et al. "Anti-hypertensive Nutraceuticals and Functional Foods" J. Agric. Food Chem. 57:4485-4499. (Year: 2009).*
Ju-Young Ko et al., "Purification and determination of two novel antioxidant peptides from flounder fish (*Paralichthys olivaceus*) using digestive proteases", Food and Chemical Toxicology 52 (2013) 113-120.

(Continued)

*Primary Examiner* — Sudhakar Katakam
*Assistant Examiner* — Zachary J Miknis
(74) *Attorney, Agent, or Firm* — Lex IP Meister, PLLC

(57) ABSTRACT

Disclosed is a pharmaceutical composition or food composition for the treatment or prevention of hypertension, containing a peptide isolated from a fraction of a flounder surimi hydrolysate as an active ingredient and is based on the finding that the flounder surimi has an effect of reducing blood pressure, and the hydrolysate of the flounder surimi, the fraction of the hydrolysate of the flounder surimi and peptides isolated from the fraction of the hydrolysate of the flounder surimi have an inhibition activity against an angiotensin I converting enzyme (ACE). Thus, peptides isolated from the fraction of the hydrolysate of the flounder surimi can be used for pharmaceutical compositions or food compositions for treating or preventing hypertension. Also, the present invention is based on the finding that the hydrolysate of the flounder surimi and peptides isolated therefrom have radical scavenging effect and a protective effect against oxidative stress and are thus capable of inhibiting ROS production, lipid peroxidation and apoptosis. Accordingly, peptides isolated from fractions of the hydrolysate of the flounder surimi can be used for food compositions for antioxidation.

2 Claims, 20 Drawing Sheets
Specification includes a Sequence Listing.

(56) References Cited

OTHER PUBLICATIONS

Bin Wang et al., "Preparation and evaluation of antioxidant peptides from ethanol-soluble proteins hydrolysate of Sphyrna lewini muscle", Peptides 36 (2012) 240-250.
Ju-Young Ko, "Small molecular preparation of flounder fish(*Paralichthys olivaceus*) muscle and its biological activities." (A Thesis for the Degree of Master of Science), Graduate School Jeju National University, 2011.

\* cited by examiner flounder surimi flounder surimi product

Molecular weight: 502.30
Amino acid sequence: Isoleucine-Valine-Aspartic acid-Arginine

SEQUENCE LISTING

<160> NUMBER OF SEQ ID NOS: 3

<210> SEQ ID NO 1
<211> LENGTH: 4
<212> TYPE: PRT
<213> ORGANISM: Paralichthys olivaceus

<400> SEQUENCE: 1

Ile Val Asp Arg
1

<210> SEQ ID NO 2
<211> LENGTH: 5
<212> TYPE: PRT
<213> ORGANISM: Paralichthys olivaceus

<400> SEQUENCE: 2

Val Ala Ser Val Ile
1               5

<210> SEQ ID NO 3
<211> LENGTH: 3
<212> TYPE: PRT
<213> ORGANISM: Paralichthys olivaceus

<400> SEQUENCE: 3

Trp Tyr Lys
1

FLOUNDER SURIMI HAVING ANTIOXIDANT AND ANTIHYPERTENSIVE EFFECTS AND METHOD OF PREPARING THE SAME

TECHNICAL FIELD

The present invention relates to a pharmaceutical composition or food composition for the treatment or prevention of hypertension containing a peptide isolated from a fraction of a hydrolysate of a flounder surimi, a flounder surimi and a flounder surimi product containing the peptide, and methods for preparing the flounder surimi and the flounder surimi product.

BACKGROUND ART

Hypertension is the most common chronic circulatory system disease occurring in 15 to 20% of adults worldwide, which is accompanied by relatively mild symptoms, but requires more active and steady care and treatment of patients because organs that function normally gradually lose functions thereof due to high blood pressure may cause fatal complications such as stroke, heart failure and coronary artery disease. The World Health Organization (WHO) defines a case where the maximum blood pressure is 160 mmHg or higher and the minimum blood pressure is 95 mmHg or higher, as hypertension. Hypertension is classified into spontaneous hypertension, the cause of which is not elucidated and secondary hypertension caused by a specific disease. More than 90% of hypertension is known to be spontaneous hypertension. More than 600 million people worldwide suffer from hypertension and 3 million people die of hypertension each year. For this reason, hypertension emerges as a global problem.

Inert angiotensin I, which is present in vivo, is transformed into angiotensin II which has vasoconstrictor activity through cleavage of C-terminal His-Leu by an angiotensin converting enzyme (ACE) to contract the blood vessels, and promotes the secretion of aldosterone in the kidney to increase body fluid levels and thereby elevate blood pressure. Thus, inhibition in the activity of ACE can lower the production of angiotensin II, which is the cause of elevation in blood pressure, thereby inhibiting increase in blood pressure.

ACE inhibitors such as enalapril and ramipril have been developed and are commercially available for suppressing hypertension. However, dysgeusia, leukocytopenia, angioedema, liver dysfunction and the like were found as side effects caused by the use of these drugs.

Thus, there has been a continuing demand for studies associated with antihypertensive effects from natural substances, and ACE inhibitors isolated from soy protein hydrolysates, chitosan and milk casein have been accepted as functional food for individual recognition by the Food and Drug Administration.

Meanwhile, when oxygen present in a stable state in vivo is transformed into reactive oxygen species (ROS) such as superoxide anion radical ($O_2^-$), hydroxyl radical ($OH^-$), hydrogen peroxide ($H_2O_2$), singlet oxygen ($^1O_2$), and the like, nonselective and irreversible destructions are induced in proteins, lipids, DNA and the like, as ingredients constituting cells in the body. As such, since oxidative stress was found to be a key cause of various diseases, research has been actively conducted to develop reactive oxygen species scavengers that are capable of effectively removing reactive oxygen species (ROS) in vivo. Particularly, there is an urgent need to develop new natural material-based reactive oxygen species scavengers that have potent reactive oxygen species scavenging activity and better safety.

There has been a continuous demand for research on the acquisition of antioxidant and antihypertensive effects from natural substances. In particular, bioactive peptides can be produced by various protein hydrolysis enzymes, and peptides derived from natural substances serve as potential physiological regulators during the metabolic process while food is digested in the intestines. In addition, antioxidant, antibacterial and antihypertensive efficacies can be expected depending on the structure, composition and amino acid sequence.

In addition, since antihypertensive and antioxidant agents, which have been produced through conventional chemical synthesis methods, were found to have problems such as side effects, efforts to obtain antihypertensive and antioxidative substances from natural substances have been continuing all over the world. In addition, in order to find new substances that can be utilized in various applications such as pharmaceuticals as well as food materials such as enzymes and health supplements, there is active research on natural living organisms, especially natural living organisms that can be easily mass-cultured and bred.

DISCLOSURE

Technical Problem

Meanwhile, marine organisms are capable of detecting a variety of novel physiologically active substances due to certain metabolic processes and unique environments that are not found in terrestrial organisms. In addition, terrestrial organisms have been actively researched, but marine organisms have not been sufficiently researched yet and they are also attracting much attention as fields having high expectation for the development of novel useful natural substances.

Technical Solution

In accordance with one aspect of the present invention, the above and other objects can be accomplished by the provision of a pharmaceutical composition for the treatment or prevention of hypertension, containing a peptide having an amino acid sequence set forth in SEQ ID NO: 1, SEQ ID NO: 2 or SEQ ID NO: 3, as an active ingredient.

In accordance with another aspect of the present invention, there is provided a food composition for the alleviation or prevention of hypertension, containing a peptide having an amino acid sequence set forth in SEQ ID NO: 1, SEQ ID NO: 2 or SEQ ID NO: 3, as an active ingredient.

In accordance with a further aspect of the present invention, there is provided a flounder surimi containing a peptide having an amino acid sequence set forth in SEQ ID NO: 1, SEQ ID NO: 2 or SEQ ID NO: 3 as an active ingredient.

In accordance with a further aspect of the present invention, there is provided a flounder surimi product containing a peptide having an amino acid sequence set forth in SEQ ID NO: 1, SEQ ID NO: 2 or SEQ ID NO: 3 as an active ingredient.

In accordance with a further aspect of the present invention, there is provided a method of producing a flounder surimi containing a peptide having an amino acid sequence set forth in SEQ ID NO: 1, SEQ ID NO: 2 or SEQ ID NO: 3 as an active ingredient, including chopping a flounder, washing the same with water, followed by refining.

In accordance with a further aspect of the present invention, there is provided a method of producing a flounder surimi product including mixing the flounder surimi obtained by the method of producing flounder surimi with table salt.

In accordance with a further aspect of the present invention, there is provided a method of preventing or treating hypertension, including administering a peptide having an amino acid sequence set forth in SEQ ID NO: 1, SEQ ID NO: 2 or SEQ ID NO: 3 to a subject.

In accordance with a further aspect of the present invention, there is provided the use of a peptide having an amino acid sequence set forth in SEQ ID NO: 1, SEQ ID NO: 2 or SEQ ID NO: 3 to a subject for the preparation of a drug for preventing or treating hypertension.

Advantageous Effects

The present invention relates to a pharmaceutical composition or food composition for the prevention or prevention of hypertension, containing a peptide isolated from a fraction of a flounder surimi hydrolysate as an active ingredient and is based on the finding that the flounder surimi has an effect of reducing blood pressure, and the hydrolysate of the flounder surimi, the fraction of the hydrolysate of the flounder surimi and peptides isolated from the fraction of the hydrolysate of the flounder surimi have an inhibition activity against an angiotensin I converting enzyme (ACE). Thus, the peptides isolated from the fraction of the hydrolysate of the flounder surimi can be used for pharmaceutical compositions or food compositions for treating or preventing hypertension.

Also, the present invention is based on the finding that the hydrolysate of the flounder surimi and peptides isolated therefrom have radical scavenging effect and a protective effect against oxidative stress and are thus capable of inhibiting ROS production, lipid peroxidation and apoptosis. Accordingly, peptides isolated from fractions of the hydrolysate of the flounder surimi can be used for food compositions for antioxidation.

BEST MODE

Figure 1:
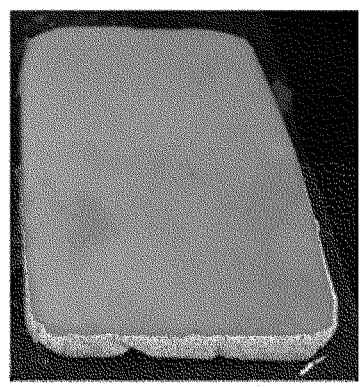
FIG. 1 illustrates a flounder surimi and a flounder surimi product.
Figure 1:
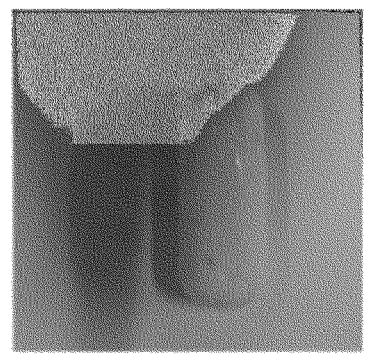

The present inventors produced a flounder surimi by chopping a flounder, washing the flounder with water, followed by refining, produced a hydrolysate of the flounder surimi using an artificial gastric fluid containing pepsin and an artificial intestinal fluid containing trypsin and alpha-chymotrypsin, and identified that fractions with different molecular weights of the hydrolysate and peptides having specific amino acid sequences isolated from the fractions have an inhibition activity against angiotensin I converting enzyme (ACE).

Accordingly, the present inventors identified that the peptides isolated from fractions of the hydrolysate of the flounder surimi can be used for pharmaceutical compositions or food compositions for treating or preventing hypertension, thus completing the present invention.

Also, the present inventors produced a flounder surimi by chopping a flounder, washing the flounder with water, followed by refining, produced a hydrolysate of the flounder surimi using an artificial gastric fluid containing pepsin and an artificial intestinal fluid containing trypsin and alpha-chymotrypsin, and identified that fractions with different molecular weights of the hydrolysate and peptides having specific amino acid sequences isolated from the fractions have a radical scavenging effect and a protective effect against oxidative stress and are thus capable of inhibiting ROS production, lipid peroxidation and apoptosis. Accordingly, the present inventors identified that the peptides isolated from fractions of the hydrolysate of the flounder surimi can be used for pharmaceutical compositions or food compositions for treating or preventing hypertension, thus completing the present invention.

In one aspect to accomplish the objects described above, the present invention is directed to a pharmaceutical composition for the treatment or prevention of hypertension, containing a peptide having an amino acid sequence set forth in SEQ ID NO: 1, SEQ ID NO: 2 or SEQ ID NO: 3, as an active ingredient.

In the present invention, the amino acid sequence set forth in SEQ ID NO: 1 is Ile-Val-Asp-Arg (IVDR), the amino acid sequence set forth in SEQ ID NO: 2 is Val-Ala-Ser-Val-Ile (VASVI), and the amino acid sequence set forth in SEQ ID NO: 3 is Trp-Tyr-Lys (WYK). The pharmaceutical composition for the treatment or prevention of hypertension contains, as an active ingredient, a peptide having the amino acid sequence set forth in SEQ ID NO: 1, that is, Ile-Val-Asp-Arg (IVDR), the amino acid sequence set forth in SEQ ID NO: 2, that is, Val-Ala-Ser-Val-Ile (VASVI), or the amino acid sequence set forth in SEQ ID NO: 3, that is, Trp-Tyr-Lys (WYK).

The peptides may be isolated from a flounder hydrolysate, more specifically, fractions of a flounder surimi hydrolysate.

The peptides may have an antioxidant activity.

The hydrolysate used herein may be a hydrolysate obtained by degrading the flounder surimi with a digestive enzyme. The digestive enzyme may be pepsin, trypsin or alpha-chymotrypsin. Accordingly, the hydrolysate of the flounder surimi according to the present invention may be the hydrolysate of pepsin, trypsin or alpha-chymotrypsin.

In one embodiment of the present invention, the flounder surimi is produced by chopping a flounder, washing the flounder with water, followed by refining. Specifically, the head, internal organs (intestines), the skin and bones are removed from a flounder originated from Jeju to obtain only flounder meat, the flounder meat is chopped with a chopper (M-12S, Korea Fuji Kogyo Co., Ltd., Korea), 0.2% polyphosphate (Na5P3O10, ES Co., Ltd., Korea) is added in an amount of 5 times the amount of the sample, the chopped flounder is immersed therein for 20 minutes, washed with the same volume of cold water to remove impurities, the flounder meat dehydrated with a dehydrator (W-110, Hanil Electric, Korea) is mixed with 4% sorbitol and 0.2% polyphosphate (LG Health care, Korea) using a Stephan mixer (774027-01, UMC 5 Electronic Co. LTD, Germany) and the resulting mixture is refined to produce the flounder surimi.

In an embodiment of the present invention, a hydrolysate of the flounder surimi was produced using an artificial gastric fluid containing pepsin and an artificial intestinal fluid containing trypsin and alpha-chymotrypsin, and it was identified that fractions with different molecular weights of the hydrolysate and the peptide having a specific amino acid sequence set forth in SEQ ID NO: 1, 2 or 3, isolated from each fraction, have an inhibition activity against angiotensin I converting enzyme (ACE).

Also, in an embodiment of the present invention, a hydrolysate of the flounder surimi was produced using an artificial gastric fluid containing pepsin and an artificial intestinal fluid containing trypsin and alpha-chymotrypsin, and it was identified that fractions with different molecular weights of the hydrolysate and the peptide having a specific amino acid sequence set forth in SEQ ID NO: 1, 2 or 3, isolated from each fraction, have radical scavenging effect and a protective effect against oxidative stress and are thus capable of inhibiting ROS production, lipid peroxidation and apoptosis.

Further, in the present invention, the fraction may be a fraction obtained by fractionating the hydrolysate of the flounder surimi on a molecular weight basis using size exclusion chromatography.

In one embodiment of the present invention, a total of three fractions was obtained by fractionating the hydrolysate of the flounder surimi on a molecular weight basis using Sephadex G-25 and size exclusion chromatography. It was found that, among them, F2 fraction had the highest ACE inhibition activity and the most potent antihypertensive activity. Three peptides having the amino acid sequences set forth in SEQ ID NOS: 1 to 3, which exhibited antihypertensive activity (ACE inhibition activity), were isolated from the F2 fraction.

Also, in one embodiment of the present invention, a total of three fractions was obtained by fractionating the hydrolysate of the flounder surimi on a molecular weight basis using Sephadex G-25 and size exclusion chromatography. It was found that, among them, F2 fraction had the best radical scavenging effect and the best antioxidant activity. Three peptides having the amino acid sequences set forth in SEQ ID NOS: 1 to 3, which exhibited antioxidant activity, were isolated from the F2 fraction.

The term "flounder" used herein is also called "flatfish", and the scientific name of the flatfish is *Paralichthys olivaceus*. The flounder has a body length of about 60 cm and a long elliptical shape that is broad in the top and bottom. It has a large mouth, well-developed teeth and eyes disposed at the left side of the body. The side where the eyes are disposed includes black and white spots distributed under a dark yellowish brown background, whereas the side where the eyes are not disposed is white. It inhabits sand or mud in the coastal area of 10-200 m depth and spawns from February to June. It appears in all coastal areas of South Korea and is found in the Kuril Islands, Japan and the South China Sea. The name "flounder" is made due to the flat body shape thereof and it can be easily distinguished from a halibut with eyes disposed on the right, due to the eyes disposed on the left.

As used herein, the term "antioxidation" means an action of suppressing oxidation. The human body has a balance between a pro-oxidant and an antioxidant. However, when the balance is broken due to various factors and oxidation is facilitated, oxidative stress is induced, which results in potential cellular damage and pathological disease. Reactive oxygen species (ROS), which is a direct cause of oxidative stress, is unstable and highly reactive and thus reacts easily with various bio-materials and attacks polymers in the body, thus causing irreversible damage to cells and tissues, or inducing mutations, cytotoxicity and carcinogenesis. Reactive nitrogen species (RNS), such as NO, $HNO_2$ and $ONOO^-$, or reactive oxygen species such as ROS, oxidize and destroy cells in the body, thus causing various diseases. In addition, the antioxidation means a function of inhibiting oxidation of cells due to highly reactive free radicals or reactive oxygen species (ROS) according to oxidative stress caused by intracellular metabolisms or ultraviolet light and includes reduction of damage to cells by eliminating free radicals or reactive oxygen species.

The angiotensin I converting enzyme (ACE) is an enzyme that functions to convert angiotensin I, decapeptide, into angiotensin II having vasoconstrictive action by cleaving a dipeptide (His-Leu) from the angiotensin I. An increase in angiotensin II strongly elevates blood pressure, promotes secretion of aldosterone, which is an antidiuretic hormone, inhibits the excretion of water and sodium, to increase circulating blood volume and thereby cause hypertension. Also, ACE degrades and inactivates bradykinin, which is a vascular relaxant, thus resulting in elevated blood pressure.

Regarding the term "hypertension" used herein, the WHO (World Health Organization) defines hypertension as a case where the maximum hypertension is not lower than 160 mmHg and the minimum hypertension is not higher than 95 mmHg. Hypertension is classified into essential (primary) hypertension, the cause of which is not found yet, and secondary hypertension caused by diseases. More than 90% of hypertension are known to be essential hypertension.

As used herein, the term "prevention" may refer to any action that inhibits or delays the onset of hypertension by administering the composition of the present invention to a subject. As used herein, the term "treatment (or therapy)" means any action that alleviates or positively affects the hypertensive symptoms by administering the composition of the present invention to a suspected hypertensive subject.

The pharmaceutical composition containing the peptides of the present invention may further contain suitable carriers, excipients or diluents conventionally used for the preparation of pharmaceutical compositions. In this case, the peptide present in the composition is not particularly limited, but may be present in an amount of 0.001% by weight to 99% by weight, preferably 0.01% by weight to 50% by weight, based on the total weight of the composition.

The pharmaceutical composition may have any one formulation selected from the group consisting of tablets, pills, powders, granules, capsules, suspensions, oral liquids, emulsions, syrups, sterilized aqueous solutions, nonaqueous solvents, freeze-drying agents and suppositories. The formulation may be any type of various oral or parenteral formulations. In the case of formulation, a diluent or excipient such as a filler, an extender, a binder, a wetting agent, a disintegrant or a surfactant is usually used.

Solid formulations for oral administration may include tablets, pills, powders, granules, capsules and the like, which may be prepared by mixing at least one excipient, for example, starch, calcium carbonate, sucrose, lactose, gelatin or the like. In addition to simple excipients, lubricants such as magnesium stearate and talc are also used. Liquid formulations for oral administration may be suspensions, oral liquids and solutions, emulsions, syrups or the like, and may include various excipients such as wetting agents, sweeteners, fragrances, preservatives and the like, in addition to water and liquid paraffin, which are simple diluents that are commonly used. Formulations for parenteral administration may be sterilized aqueous solutions, nonaqueous solvents, suspensions, emulsions, freeze-drying agents and suppositories. Examples of the nonaqueous solvents and suspensions include propylene glycol, polyethylene glycol, vegetable oil such as olive oil, injectable ester such as ethyl oleate, and the like. Examples of the suppository base include Witepsol, macrogol, Tween 61, cacao butter, laurin butter, glycerogelatin and the like.

The pharmaceutical composition of the present invention may be administered in a pharmaceutically effective amount. As used herein, the term "pharmaceutically effective amount" refers to an amount of a pharmaceutical composition which is sufficient to treat or prevent diseases at a reasonable benefit/risk ratio applicable to all medical treatments or preventions. The effective amount level may be changed depending on a variety of factors including the type, severity, age, and gender of the subject, the type of disease, activity of drug, sensitivity of the subject to the drug, administration time, administration route, excretion rate and treatment period, and drugs used in combination with the composition according to the present invention, and other factors well-known in the art. The pharmaceutical composition of the present invention may be administered alone or in combination with other therapeutics. In this case, the pharmaceutical composition of the present invention may be administered sequentially or simultaneously with conventional therapeutics. In addition, the pharmaceutical composition may be administered in single or multiple doses. It is important to administer the minimal amount sufficient to achieve the maximum efficacy without side effects, while thoroughly taking into consideration these factors. Such an amount can be easily determined by those skilled in the art.

The pharmaceutical composition of the present invention can be applied to any subject without any particular limitation as long as the subject needs treatment of hypertension. Examples of the subject include non-human animals such as monkeys, dogs, cats, rabbits, marmots, rats, mice, cattle, sheep, pigs and goats, humans, birds and fish. The pharmaceutical composition may be administered non-orally, subcutaneously, intraperitoneally, intrapulmonarily, or intranasally, and may be administered by a suitable method, including intralesional administration, if necessary, for local treatment. The preferred dosage of the pharmaceutical composition of the present invention varies depending on the condition and the weight of the subject, the severity of disease, the type of drug, the route of administration and the period of administration, but can be appropriately selected by those skilled in the art. For example, the pharmaceutical composition may be administered by oral, rectal or intravenous, intramuscular, subcutaneous, intrauterine cervical or intracerebrovascular injection, but the present invention is not limited thereto.

A suitable total daily dose may be determined by a physician within the scope of reasonable medical judgment and is generally 0.001 to 1,000 mg/kg, preferably 0.05 to 200 mg/kg, more preferably 0.1 to 100 mg/kg, may be administered in single or multiple doses per day.

In another aspect of the present invention, the present invention is directed to a food composition for the alleviation or prevention of hypertension, containing a peptide having an amino acid sequence set forth in SEQ ID NO: 1, SEQ ID NO: 2 or SEQ ID NO: 3 as an active ingredient.

In the present invention, the amino acid sequence set forth in SEQ ID NO: 1 is Ile-Val-Asp-Arg (IVDR), the amino acid sequence set forth in SEQ ID NO: 2 is Val-Ala-Ser-Val-Ile (VASVI), and the amino acid sequence set forth in SEQ ID NO: 3 is Trp-Tyr-Lys (WYK). The pharmaceutical composition for the treatment or prevention of hypertension contains, as an active ingredient, a peptide having the amino acid sequence set forth in SEQ ID NO: 1, that is, Ile-Val-Asp-Arg (IVDR), the amino acid sequence set forth in SEQ ID NO: 2, that is, Val-Ala-Ser-Val-Ile (VASVI), or the amino acid sequence set forth in SEQ ID NO: 3, that is, Trp-Tyr-Lys (WYK).

The peptides may be isolated from a flounder hydrolysate, more specifically, fractions of a flounder surimi hydrolysate.

The peptides may have an antioxidant activity.

In the present invention, the peptides, hypertension, flounder, flounder surimi, hydrolysate, antioxidation and prevention are as described above.

As used herein, the term "alleviation" means any action that reduces or positively affects the hypertensive symptoms by administering the composition of the present invention to a subject suspected of having hypertension or having hypertension that is prevented or treated using the peptide having the amino acid sequence set forth in SEQ ID NO: 1, SEQ ID NO: 2 or SEQ ID NO: 3.

Specifically, the peptide having the amino acid sequence set forth in SEQ ID NO: 1, SEQ ID NO: 2 or SEQ ID NO: 3 can be administered to a food composition for the alleviation or prevention of hypertension.

The food composition of the present invention may be in the form of a pill, a powder, a granule, an infusion, a tablet, a capsule or a liquid. The type of food, to which the peptides of the present invention can be added, is not particularly limited, and examples thereof include drinks, gums, teas, vitamin complexes, health supplement foods and the like.

In addition to the peptide having the amino acid sequence shown in SEQ ID NO: 1, SEQ ID NO: 2 or SEQ ID NO: 3, the food composition may contain other components and the type thereof is not particularly limited. For example, like ordinary food, the food composition may contain various herbal medicine extracts, cytologically acceptable food supplementary additives or natural carbohydrates, but the present invention is not limited thereto.

As used herein, the term "food supplementary additive" means a component which can be added to food in a supplementary manner, and is added to produce health functional food of each formulation and can be appropriately selected and used by those skilled in the art. Examples of the food supplementary additive include various nutrients, vitamins, minerals (electrolytes), flavors such as synthetic flavors and natural flavors, colorants, fillers, pectic acid and salts thereof, alginic acid and salts thereof, organic acids, protective colloidal thickeners, pH adjusters, stabilizers, preservatives, glycerin, alcohols, carbonating agents used in carbonated drinks and the like. However, the types of the food supplementary additive of the present invention are not limited by these examples.

Examples of the natural carbohydrate include: monosaccharides such as glucose and fructose; disaccharides such as maltose and sucrose; polysaccharides such as dextrin and cyclodextrin; and sugar alcohols such as xylitol, sorbitol and erythritol. In addition to those described above, natural flavors (such as thaumatin), stevia extracts (such as rebaudioside A or glycyrrhizin) and synthetic flavors (such as saccharin, aspartame) can be advantageously used.

The food composition of the present invention may contain a health functional food. In the present invention, the food composition may be a health functional food. As used herein, the term "health functional food" refers to a food which is prepared and processed in the form of a tablet, capsule, powder, granule, liquid or pill from raw materials or components having functionalities useful for the human body. Here, the term "functionalities" means that nutrients are controlled for the structures and functions of the human body or the effects useful for the hygiene application such as physiological activity is obtained. The health functional food of the present invention can be prepared by a method commonly used in the art and can be prepared by adding raw materials and ingredients conventionally added in the art. Also, unlike general medicines, the present invention contains food as a raw material, thus having advantages of being free from side effects that may occur when a drug is administered for a long time, and having excellent portability.

The amount of the active ingredient to be mixed can be suitably determined according to the intended use (prevention, health or therapeutic treatment). In general, the peptide of the present invention may be added in an amount of 1 to 50% by weight, preferably 5 to 10% by weight, in the preparation of food, but the present invention is not limited thereto. However, in the case of long-term administration intended for health and hygiene purposes or for controlling health, the amount can also be not higher than the range defined above.

There is no particular limitation on the kind of the food. Examples of the food to which the substance can be added include dairy products including surimi, surimi products, sausages, bread, chocolates, candies, snacks, confectionery, pizza, ramen, other noodles, gums, ice cream, various soups, beverages, drinks, alcoholic beverages, vitamin complexes and the like, all of which include health functional foods in a conventional sense.

In another aspect, the present invention is directed to a flounder surimi containing a peptide having an amino acid sequence set forth in SEQ ID NO: 1, SEQ ID NO: 2 or SEQ ID NO: 3 as an active ingredient.

The surimi is obtained by removing the skin, internal organs and bones from fish, washing the remaining meat with cold water several times, dehydrating the same and mixing the same with sugar and phosphate.

In one embodiment of the present invention, a flounder surimi is produced by chopping a flounder, washing the same with water, followed by refining.

As described above, it is found that peptides having the amino acid sequences set forth in SEQ ID NOS: 1 to 3 are present in the fractions of the hydrolysate of the flounder surimi. That is, the peptides having the amino acid sequences set forth in SEQ ID NOS: 1 to 3 are present in the flounder surimi as well. Accordingly, the present invention can provide a flounder surimi containing a peptide having an amino acid sequence set forth in SEQ ID NO: 1, SEQ ID NO: 2 or SEQ ID NO: 3 as an active ingredient.

In another aspect, the present invention is directed to a flounder surimi product containing a peptide having an amino acid sequence set forth in SEQ ID NO: 1, SEQ ID NO: 2 or SEQ ID NO: 3 as an active ingredient.

In one embodiment of the present invention, the flounder surimi is produced by chopping a flounder, washing the same with water, followed by refining. Specifically, the produced flounder surimi is frozen, the frozen surimi is thawed at a low temperature and primarily ground using a Stephan mixer for 20 minutes, 2% table salt was added thereto, the resulting surimi is secondarily ground for 20 minutes, 2% starch was added thereto and the resulting surimi is thirdly ground for 20 minutes. Then, the resulting surimi is injected into a cylindrical polyethylene bag with a diameter of 2 cm, cased and naturally coagulated for 24 hours to produce the flounder surimi product.

The term "flounder surimi product" generally refers to food which is prepared by adding a salt to fish meat, followed by molding and heating, and includes fish cake, fried fish cake, roasted fish cake, fish ham and sausage.

As described above, it is found that peptides having the amino acid sequences set forth in SEQ ID NOS: 1 to 3 are present in the fractions of the hydrolysate of the flounder surimi. That is, the peptides having the amino acid sequences set forth in SEQ ID NOS: 1 to 3 are present in the flounder surimi product obtained by mixing the flounder surimi with table salt. Accordingly, the present invention can provide a flounder surimi product containing a peptide having an amino acid sequence set forth in SEQ ID NO: 1, SEQ ID NO: 2 or SEQ ID NO: 3 as an active ingredient.

In another aspect, the present invention is directed to a method of producing a flounder surimi containing a peptide having an amino acid sequence set forth in SEQ ID NO: 1, SEQ ID NO: 2 or SEQ ID NO: 3, as an active ingredient, including chopping a flounder, washing the same with water, followed by refining.

In the present invention, the SEQ ID NO: 1, the SEQ ID NO: 2, the SEQ ID NO: 3, the peptide, the flounder, the flounder surimi, and the method of producing the flounder surimi are as described above.

In another aspect, the present invention is directed to a method of producing a flounder surimi product including mixing the flounder surimi produced by the method of producing the flounder surimi with table salt.

In the present invention, the SEQ ID NO: 1, the SEQ ID NO: 2, the SEQ ID NO: 3, the peptide, the flounder, the flounder surimi, the flounder surimi product and the method of producing the flounder surimi product are as described above.

In another aspect, the present invention is directed to a method of preventing or treating hypertension, including administering the peptide having an amino acid sequence set forth in SEQ ID NO: 1, SEQ ID NO: 2 or SEQ ID NO: 3 to a subject.

In the present invention, the terms "peptide having an amino acid sequence set forth in SEQ ID NO: 1, SEQ ID NO: 2 or SEQ ID NO: 3", "hypertension", "prevention" and "treatment" are as described above.

As used herein, the term "subject" means all animals including humans suffering from hypertension. The subject includes mammals such as cattle, pigs, sheep, chickens, dogs and humans, birds and the like, and includes, without limitation, any subject that undergoes treatment or prevention of hypertension through administration with the peptide having an amino acid sequence set forth in SEQ ID NO: 1, SEQ ID NO: 2 or SEQ ID NO: 3.

In another aspect, the present invention is directed to the use of the peptide having an amino acid sequence set forth in SEQ ID NO: 1, SEQ ID NO: 2 or SEQ ID NO: 3 for the preparation of a drug for preventing or treating hypertension.

In the present invention, the terms "peptide having an amino acid sequence set forth in SEQ ID NO: 1, SEQ ID NO: 2 or SEQ ID NO: 3", "hypertension", "prevention" and "treatment" are as described above.

MODE FOR INVENTION

Hereinafter, embodiments of the present invention will be described in detail with reference to the accompanying drawings so that those skilled in the art can easily carry out the present invention. However, the present invention may be embodied in many different forms and are not limited to the embodiments set forth herein.

<A. Measurement of Antihypertensive Effect>

Example 1: Purchase of Raw Materials and Production of Surimi and Surimi Products The surimi used for the present invention was produced as follows. The head, internal organs (intestines), the skin and bones were removed from a flounder originated from Jeju to obtain only flounder meat, the flounder meat was chopped with a chopper (M-12S, Korea Fuji Kogyo Co., Ltd., Korea), 0.2% polyphosphate (Na5P3O10, ES Co., Ltd., Korea) was added in an amount of 5 times the amount of the sample, and the chopped flounder was immersed therein for 20 minutes and washed with the same volume of cold water and the water used for washing was removed four times. Then, the residue was screened to remove other impurities and then dehydrated with a dehydrator (W-110, Hanil Electric, Korea). The dehydrated surimi was mixed with 4% sorbitol (LG Health care, Korea), 4% sugar (CJ CheilJedang Corporation, Korea) and 0.2% polyphosphate using a Stephan mixer (774027-01, UMC 5 Electronic Co. LTD, Germany) and the resulting mixture was stored in 500 g in a case at −70° C. The flounder surimi product was produced as follows. The frozen flounder surimi was thawed at a low temperature of 4° C. and primarily ground using a Stephan mixer for 20 minutes, 2% table salt was added thereto, the resulting surimi was secondarily ground for 20 minutes, 2% starch was added thereto and the resulting surimi was thirdly ground for 20 minutes. Then, the resulting surimi was injected into a cylindrical polyethylene bag with a diameter of 2 cm, cased and naturally coagulated at 4° C. for 24 hours. Then, the resulting surimi was heated at 85° C. in a water bath for 30 minutes and cooled at a low temperature. Then, physical properties of the resulting surimi product were tested. FIG. 1 shows the flounder surimi and flounder surimi product produced by the method described above.

Example 2: Analysis of Physicochemical Properties of Surimi and Surimi Product Produced Using Flounder 1) Analysis of General Ingredient Content General ingredients were measured according to the AOAC method (1995), moisture was measured by an atmospheric pressure heating drying method, crude protein was measured by a semimicro-kjeldahl method, crude ash was measured by a dry asking method and crude fat was measured by an Soxhlet method. Total mercury in the heavy metals was analyzed by a combustion gold amalgamation method using a mercury analyzer (SP-3A, Nippon Instrument Co., Tokyo, Japan) after lyophilization of a sample and lead was analyzed in a sample prepared by wet-degrading an organic substance with nitric acid, using an inductively coupled plasma spectrophotometer (ICP) (Atomscan 25, TJA, USA).

2) Analysis of Constituent Amino Acids

Analysis of constituent amino acids was carried out using Agilent 6890N GC-FID and analytical conditions were as follows: Column: ZB-AAA (10 meter×0.25 mm), inlet temperature: 250° C., temperature: 110° C. to 320° C., detector: 320° C., injection volume: 2 μl, split ratio 5:1, carrier gas: nitrogen, 1.5 mL/min. Amino acid standard produced by Phenomenex Corp. was used as the standard solution.

Example 3: Analysis of Physical Properties of Surimi and Surimi Product Produced Using Flounder 1) Measurement of Whiteness Whiteness was measured with a direct color meter (NE4000, Nippon Denshoku Industries Co., Japan) with slight modification of the method mentioned by Park (1994). The whiteness was determined by measuring Hunter L, a and b values of a thawed surimi injected into a container and of a sample having a shear surface with a predetermined size of 2.5 cm×2.5 cm horizontally cut from a circular fish cake (surimi product). At this time, for the standard white plate of the direct color meter, the L value was 100.05, the a value was −0.03, and the b value was 0.01.

2) Measurement of Gel Strength

The gel strength was measured with slight modification of the method of Okada (1963), and the sample was obtained by cutting a circular fish cake (surimi product) into a predetermined size (2.5×2.5 cm). That is, gel strength was expressed in "load×depth" after measuring the load and depth of the sample using a Sun rheometer (COMPAC-100, Sun Scientific Co., Japan). At this time, the load of the rheometer was 1 kg, the speed of the plunger was 20 mm/min, and the plunger used herein was a circular plunger with a diameter of 5 mm.

Example 4: Measurement of Physiological Activity Upon Consumption of Flounder Surimi Product 1) Production of Artificial Digestive Fluids and Treatment Therewith The artificial gastric fluid and artificial intestinal fluid used for an artificial digestion model were obtained by slightly modifying the method of Hur (2011), and the compositions thereof are shown in Table 1. 1 L of an artificial gastric fluid was added to 500 g of the flounder surimi, the pH was adjusted to 1.5, and the mixture was stirred at 37° C. for 4 hours. Then, pH was adjusted to 8, 1 L of an artificial intestinal fluid was added thereto and the resulting mixture was stirred again at 37° C. for 4 hours. Then, the enzyme was inactivated at 95° C., the residue was removed and the resulting flounder surimi was used in the experiment.

TABLE 1

Composition of in vitro gastric fluid

| | Artificial gastric fluid | Artificial intestinal fluid |
|---|---|---|
| Inorganic solution | 15.7 mL NaCl 175.3 g/L<br>3.0 mL NaH$_2$PO$_4$ 88.8 g/L<br>9.2 mL KCl 89.6 g/L<br>18 mL CaCl$_2$•2H$_2$O 22.2 g/L<br>10 mL NH$_4$Cl 30.6 g/L<br>6.5 mL HCl 3.7% g/g | 40 mL NaCl 175.3 g/L<br>40 mL NaHCO$_3$ 84.7 g/L<br>10 mL KH$_2$PO$_4$ 8 g/L<br>6.3 mL KCl 89.6 g/L<br>10 ml MgCl$_2$ 5 g/L<br>180 µl HCl 37% g/g |
| Organic solution | 10 mL glucose 65 g/L<br>10 mL glucuronic acid 2 g/L<br>10 mL glucosamine hydrochloride 33 g/L | |
| Enzyme and etc | 2.5 g Pepsin<br>907.6 mL DW | 9 ml CaCl$_2$•2H$_2$O$_2$ 22.2 g/L<br>8 g Trypsin<br>2 g a-Chymotrypsin<br>884.52 mL DW |

2) ACE Inhibition Activity

ACE inhibition activity was measured by a modified version of Cushman and Cheung's method. The crude enzyme solution used herein was the supernatant obtained by centrifuging (4° C., 4,000 rpm, 40 min) after extracting a rabbit lung acetone powder (Sigma-Aldrich Co.) at a concentration of 0.2 g/10 mL (w/v) and at 4° C. for 24 hours. The substrate was prepared by dissolving hippurylhistidyl-leucine (HLL, Sigma-Aldrich Co.) at a concentration of 5 mg/mL (w/v) in a 0.1 M sodium borate buffer (pH 8.3) containing 0.3 M NaCl.

ACE inhibition activity was determined as follows. 50 µL of an ACE enzyme solution was added to 50 µL of a sample extract, reaction was proceeded at 37° C. for 5 minutes, 50 µL of a substrate was added thereto and the reaction was proceeded at 37° C. for 1 hour. Then, 150 µL of 1N HCl was added to stop the reaction, 750 µL of ethyl acetate was added thereto, and the mixture was stirred for 1 minute and centrifuged (3,500 rpm, 10 min) to obtain 500 µL of the supernatant. The supernatant was completely dried at 105° C. for 4 hours, 2 mL of ethyl acetate was added thereto, and the absorbance was measured at 228 nm. A control group was obtained by adding 50 µL of distilled water, instead of the sample extract.

3) Identification of NO Production Effect of Blood Vessels

In order to identify the NO production effect of blood vessels, 1×10$^5$ vascular endothelial cells (HUVEC cells) were seeded in a 96-well plate. 24 hours later, the medium of each well was changed from growth medium to a base medium. After 2 hours, the cells were treated with the sample and immediately treated with 10 µl of 300 µM DAF-FM-DA (Sigma, USA). After 1 hour 30 minutes, the fluorescence value was measured.

4) Measurement of Blood Pressure Change

The changes in blood pressure were measured after feeding the flounder surimi to spontaneously hypertensive rats (SHR). Specifically, 50 to 300 g SHR was fed with mg/kg of a lyophilized flounder surimi kneaded in water, and changes in blood pressure were measured by the tail-cuff method using a CODA™ blood pressure monitor (Kent Scientific Corp., Torrington, Conn., USA) at 0, 3, 6 and 9 hours.

Experimental Example 1. Analysis of Contents of General Components and Heavy Metals of Surimi Obtained from Flounder The frozen surimi was produced using flounder, fish used for the present invention and general ingredient analysis results of the produced surimi are shown in Table 2. The results showed that the moisture content of the flounder surimi product was 73.18% and the protein content was 18.93%.

TABLE 2

Analysis of contents of general components of surimi produced from flounder

| | General ingredient (g/100 g) | | | | |
|---|---|---|---|---|---|
| Surimi | Moisture | Protein | Carbohydrate | Fat | Ash |
| Flounder surimi | 73.18 ± 0.26 | 18.93 ± 0.98 | 7.68 ± 0.65 | 0.11 ± 0.03 | 0.10 ± 0.00 |

In case of the standard heavy metal content for surimi, for surimi produced from freshwater fish and shellfish, the standard heavy metal content is defined as 10.0 mg/kg or less. In case of mercury content, for surimi produced from sea fish and shellfish (excluding deep sea fish and shellfish, and tuna), the total mercury is regulated as 0.5 mg/kg or less. For surimi produced from sea fish and shellfish (excluding deep sea fish and shellfish, and tuna), the lead content is regulated as 2.0 mg/kg or less.

The result of analysis of the heavy metal contents of the flounder surimi showed that lead, cadmium and arsenic were not detected from the flounder surimi and mercury was 0.02 mg/kg, which is below the reference value, as shown in Table 3.

TABLE 3

Heavy metal contents of surimi produced from flounder

| | Heavy metal contents (ppm) | | | |
|---|---|---|---|---|
| | Lead (Pb) | Cadmium (Cd) | Mercury (Hg) | Arsenic (As) |
| Flounder surimi | not detected | not detected | 0.02 ± 0.00 | not detected |
| SA-grade commercially available pollack surimi | — | — | 0.01 ± 0.00 | — |

Experimental Example 2: Analysis of Constituent Amino Acids in Frozen Flounder Surimi 1 L of an artificial gastric fluid was added to 500 g of a flounder surimi, the pH was adjusted to 1.5, and the mixture was stirred at 37° C. for 4 hours. Then the pH was adjusted to 8, 1 L of an artificial intestinal fluid was added thereto and the mixture was stirred again at 37° C. for 4 hours. Then, the enzyme was inactivated at 95° C., the residue was removed and the resulting flounder surimi was used in the experiment.

Table 4 shows the results of analysis of constituent amino acids of the flounder surimi and flounder surimi hydrolysate. Leucine, glutamic acid and lysine, which are major amino acids having higher contents, did not change. The content of lysine was decreased after hydrolysis and cystine was detected after hydrolysis.

TABLE 4

Constituent amino acids of flounder

| | Flounder surimi | Flounder surimi hydrolysate |
|---|---|---|
| Alanine | 11570 (2.52) | 7926 (3.02) |
| Glycine | 8710 (1.89) | 6398 (2.45) |
| Valine | 19866 (4.33) | 14619 (5.59) |
| Noraline | — | 2459 (0.96) |
| Leucine | 47553 (10.35) | 28789 (11.02) |
| Isoleucine | 18951 (4.13) | 10680 (4.09) |
| Threonine | 7818 (1.70) | 5660 (2.18) |
| Serine | 5661 (1.24) | 4497 (1.72) |
| Proline | 7164 (1.57) | 5017 (1.91) |
| Aspartic acid | 28490 (6.20) | 15290 (5.86) |
| Methionine | 10656 (2.33) | 4248 (1.61) |
| 4-Hydroxyproline | — | — |
| Glutamic acid | 51177 (11.14) | 26597 (10.18) |
| Phenylalanine | 41741 (9.07) | 24203 (9.26) |
| Lysine | 135164 (29.41) | 66251 (25.37) |
| Histidine | 34825 (7.57) | 18136 (6.93) |
| Hydroxylysine | — | — |
| Tyrosine | 30097 (6.55) | 17916 (6.85) |
| Cystine | — | 2650 (1.00) |

Experimental Example 3: Whiteness of Frozen Flounder Surimi

The common Asian criteria for frozen surimi include items of moisture content, gel strength, shear deformation, elasticity sensory test and whiteness. Among them, whiteness is not lower than 45 in grade A, not lower than 47 in grade SA, and not lower than 49 in grade 3A. Therefore, whiteness is an important item that determines the grade of frozen surimi and surimi having high whiteness is used as a premium material for premium surimi products. According to the results of research by Heu (2010), SA, FA, AA, A, KA, KB and RA grades are generally used in the market and these grades show that as the whiteness becomes higher, the grade of surimi becomes higher.

The flounder surimi has a high whiteness of 63.6 which is higher than that of SA-grade commercially available surimi.

TABLE 5

Whiteness of surimi prepared with *Paralichthys olivaceus*

| | Whiteness | | |
|---|---|---|---|
| | L (Whiteness) | a (Redness) | b (Yellowness) |
| Flounder surimi | 63.60 ± 0.98 | 0.13 ± 0.01 | 1.18 ± 0.03 |
| SA-grade commercially available pollack surimi | 54.70 ± 1.13 | −0.74 ± 0.09 | 9.38 ± 0.09 |

Experimental Example 4: Whiteness and Gel Strength of Flounder Surimi Product The gel strength of a surimi product is an important factor that determines the grade of the surimi product and is evaluated as a factor to increase the taste (mouthfeel) of the surimi product. Research by Heu (2010) reported that the gel strengths of a pollack surimi product were 945.2 g×cm for SA grade, 782.0 g×cm for FA grade, 747.3 g×cm for AA grade, 611.1 g×cm for A grade, 628.1 g×cm for KA grade, 444.5 g×cm for KB grade, and 256.8 g×cm for RA grade, respectively, and gel strength is different depending on the grade of surimi product.

The gel strength of the pollack surimi product was 1,012 g×cm which was similar to that of SA grade and gel strength is slightly changed depending on production conditions of the surimi product.

The flounder surimi product had a gel strength of 1,064 g×cm. Also, since protein is readily denatured after heating and cooling processes, the color may be deteriorated through heating and cooking processes. Thus, whiteness was measured again after production of the flounder surimi product. The results showed that there was a significant difference between the whiteness of the flounder surimi before cooking and the whiteness of the flounder surimi product after cooking, and the whiteness of the flounder surimi product was 89.32 which was higher than that of the pollack surimi product.

TABLE 6

| | Hunter color system | | | |
|---|---|---|---|---|
| Surimi | L (Whiteness) | A (Redness) | B (Yellowness) | Gel strength (g × cm) |
| Flounder surimi product | 89.32 ± 1.26 | 1.22 ± 0.23 | 11.82 ± 0.89 | 1064 ± 8.63 |
| SA-grade commercially available pollack surimi product | 63.60 ± 1.23 | 1.42 ± 0.36 | 4.39 ± 1.10 | 1012 ± 11.3 |

Figure 2:
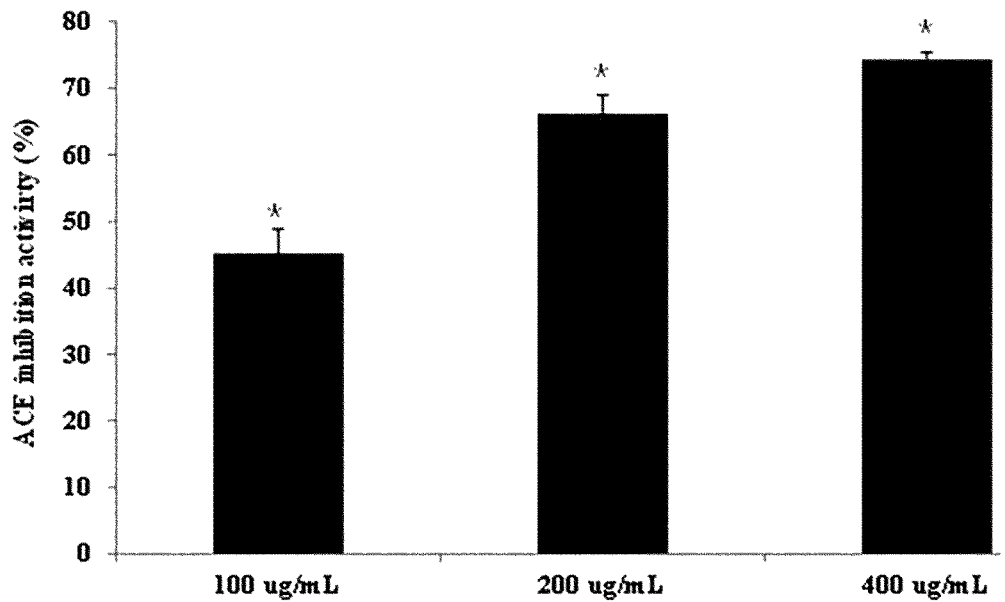
FIG. 2 shows the ACE inhibition activity of the flounder surimi hydrolysate.

Experimental Example 5: Measurement of Physiological Activity Upon Consumption of Flounder Surimi Product a) ACE Inhibition Effect of Flounder Surimi Hydrolysate Angiotensinogen is converted to angiotensin I by renin and angiotensin I is converted to angiotensin II by an angiotensin converting enzyme (ACE). It is known that the angiotensin I converting enzyme (ACE) induces hypertension. It is known that hypertension can be inhibited through inhibition of ACE, which functions to convert angiotensin I to angiotensin II. Therefore, the ACE inhibition activity of the flounder surimi hydrolysate was measured and is shown in FIG. 2. FIG. 2 shows the ACE inhibition activity of the flounder surimi hydrolysate. The results showed that the ACE inhibition rate was significantly increased as the concentration of the hydrolysate increased.

(B) NO Production Effect of Flounder Surimi Product Hydrolysate in HUVEC

Figure 3:
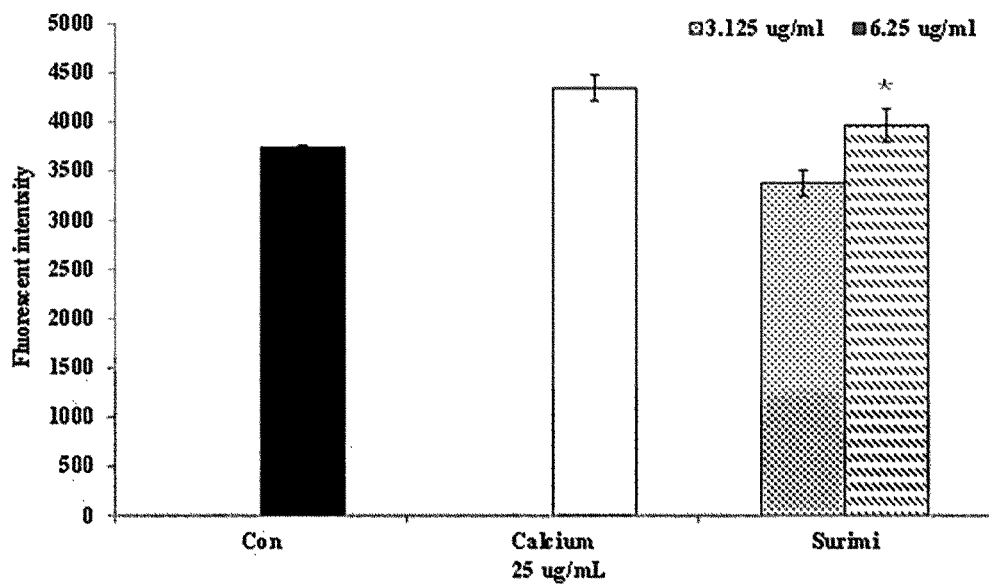
FIG. 3 shows the NO production effect of the flounder surimi hydrolysate in vascular endothelial cells.

It is known that NO production in vascular endothelial cells (HUVEC) causes blood vessels to be relaxed, resulting in alleviation of hypertension. Thus, changes in NO production were measured after treating with the flounder surimi product hydrolysate (FIG. 3). FIG. 3 shows the NO production effect of the flounder surimi hydrolysate. The result showed that NO production was significantly increased at a flounder surimi hydrolysate concentration of 6.25 μl/ml and that hypertension could be suppressed when the flounder surimi product was consumed.

(C) Measurement of Blood Pressure Changes when Feeding Flounder Surimi to Spontaneously Hypertensive Rats (SHR)

Hypertension and hyperlipidemia are major risk factors for cardiovascular diseases, such as coronary artery disease, myocardial infarction and stroke, and their incidence rate is increasing. Hypertension is the most common chronic cardiovascular disease, and in particular, spontaneous hypertension, the cause of which is unknown, accounts for 90% of total hypertension. SHR is a white rat that has hypertension at 6-10 weeks of age and maintains a systolic blood pressure of 200 mmHg or higher. The cause of blood pressure increase in SHR is unclear and thus SHR has been widely used in the study of the mechanism of spontaneous hypertension in humans.

Figure 4:
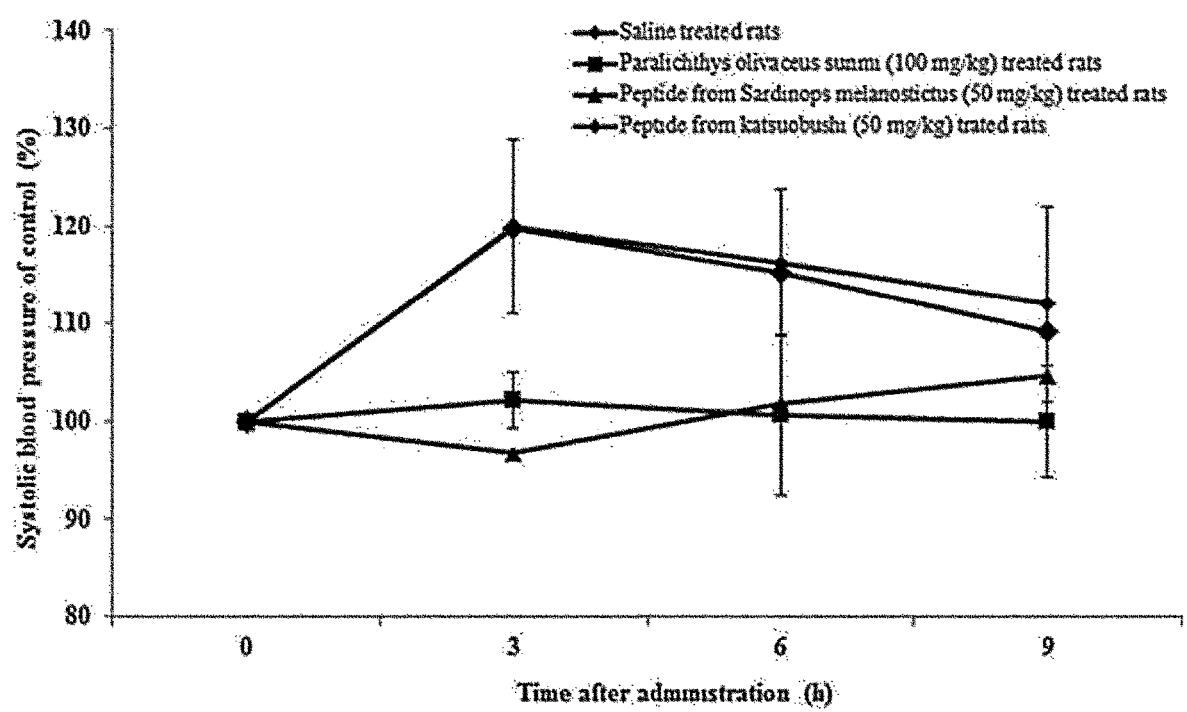
FIG. 4 shows changes in blood pressure after feeding the flounder surimi to spontaneously hypertensive rats (SHR)

Therefore, in the present invention, the change in blood pressure after feeding the flounder surimi to the SHR is shown in FIG. 4. FIG. 4 shows changes in blood pressure after feeding the flounder surimi to spontaneously hypertensive rats (SHRs). The result showed that, when the systolic blood pressure was measured 3 hours after feeding the flounder surimi, the saline-fed group showed a 31% increase in the systolic blood pressure, while the flounder surimi-fed group showed a only 2% increase in the systolic blood pressure, which corresponds to a 29% decrease in the blood pressure. For reference, peptides isolated from Katsuobushi and sardinops melanostictus were used as positive controls.

D) Isolation of Peptides Having Antihypertensive Activity Derived from Flounder Surimi Hydrolysate Using Sephadex G-25 Column.

Figure 5:
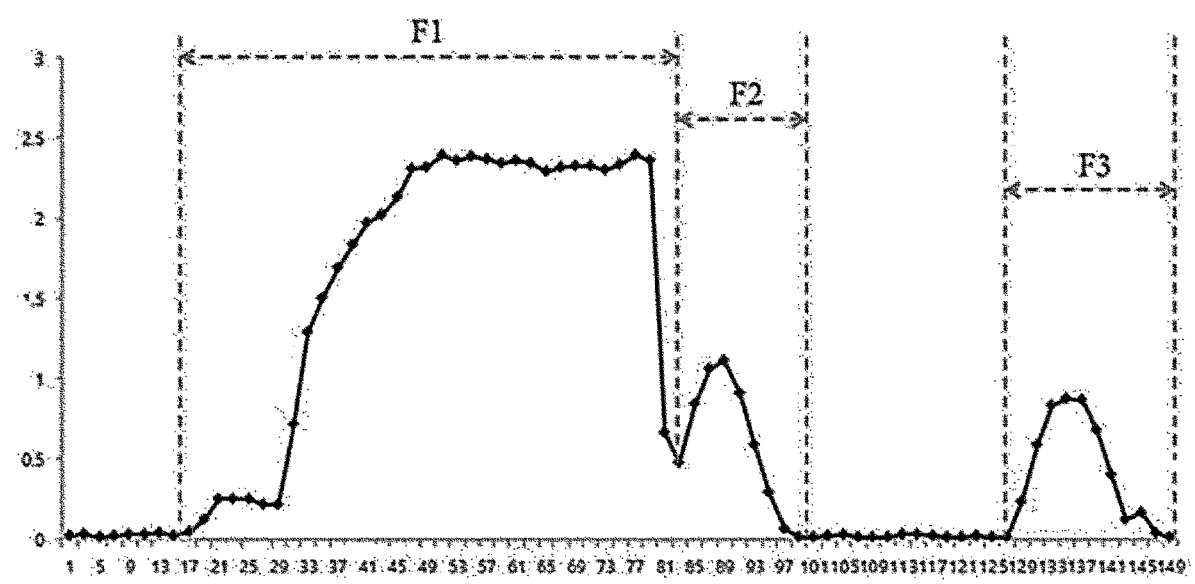
FIG. 5 shows the results of size exclusion chromatography of the flounder surimi hydrolysate using a Sephadex G-25 column.
Figure 6:
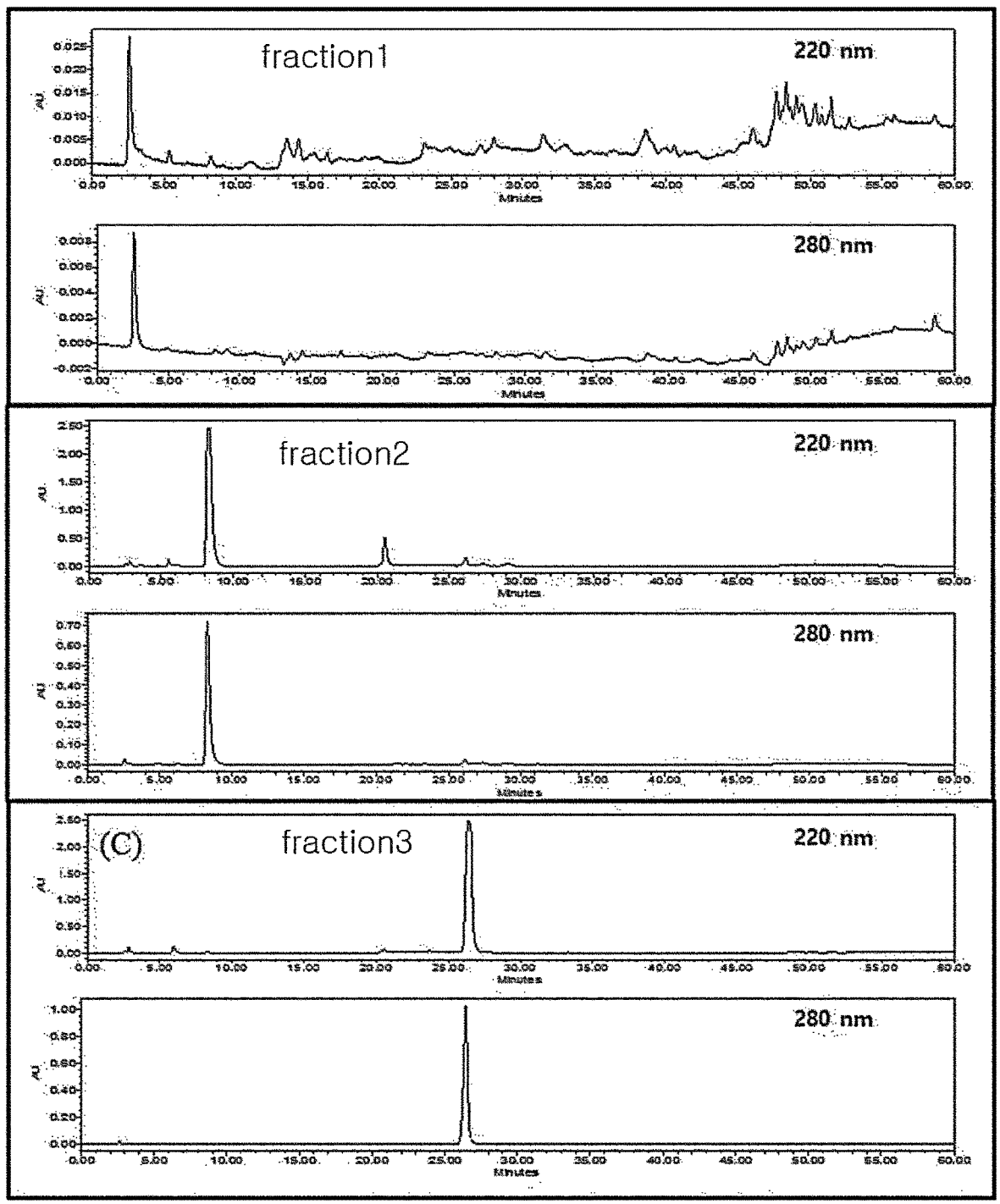
FIG. 6 shows the results of reverse phase chromatograms of fractions of the flounder surimi hydrolysate.

A total of three fractions was obtained on a molecular weight basis from the flounder surimi hydrolysate using Sephadex G-25 and size exclusion chromatography. FIG. 5 shows the results of size exclusion chromatography of the flounder surimi hydrolysate using a Sephadex G-25 column. The reverse phase chromatograms of the respective fractions are shown in FIG. 6, and the respective fractions were measured at wavelengths of 220 nm and 280 nm. Fraction 1 was considered to contain great amounts of substances since considerably many peaks were detected therefrom. Fraction 2 had a purity of 90% or more since in addition to one main peak, a small number of peaks were detected therefrom. Fraction 3 showed a purity of 95% or more since only one main peak was detected therefrom.

E) Measurement of ACE Inhibition Activity of Size-Exclusion Chromatography Fractions The ACE inhibition activity of the three fractions obtained using Sephadex G-25 was measured. As can be seen from Table 7, Fraction 1 contained proteins exceeding 5 kDa, Fraction 2 contained proteins not more than 1 kDa, and Fraction 3 contained proteins less than 1 kDa.

TABLE 7

|  | Molecular weight | ACE inhibition (%) |
|---|---|---|
| Fraction 1 | >5 kDa | 4.3% ± 0.18 |
| Fraction 2 | ≤1 kDa | 65% ± 0.93 |
| Fraction 3 | <1 kDa | 62% ± 2.68 |

Figure 7:
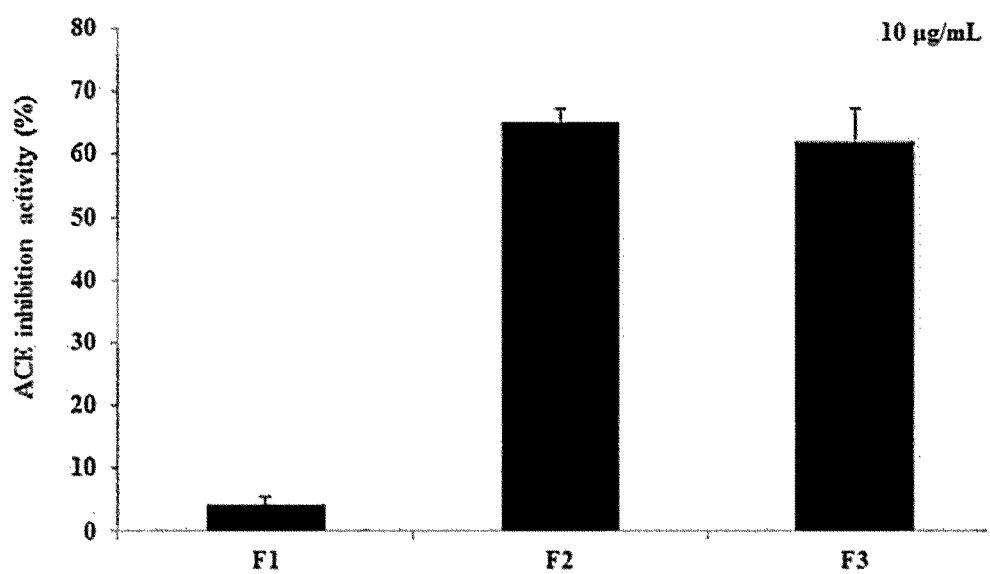
FIG. 7 shows the ACE inhibition activity of the size exclusion chromatography fractions using Sephadex G-25.

FIG. 7 shows the ACE inhibition activity of the size exclusion chromatography fractions using Sephadex G-25. The result showed that Fractions F2 and F3 showed excellent ACE inhibition activity.

Figure 8:
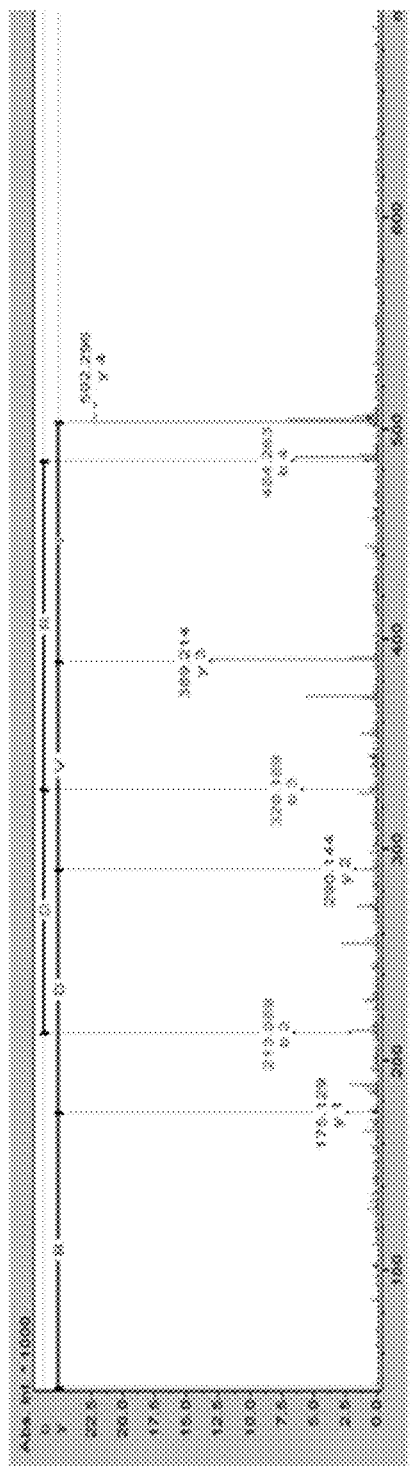
FIG. 8 shows the amino acid sequence, Ile-Val-Asp-Arg (IVDR), of the peptide derived from Fraction 2 and the molecular weight thereof.
Figure 9:
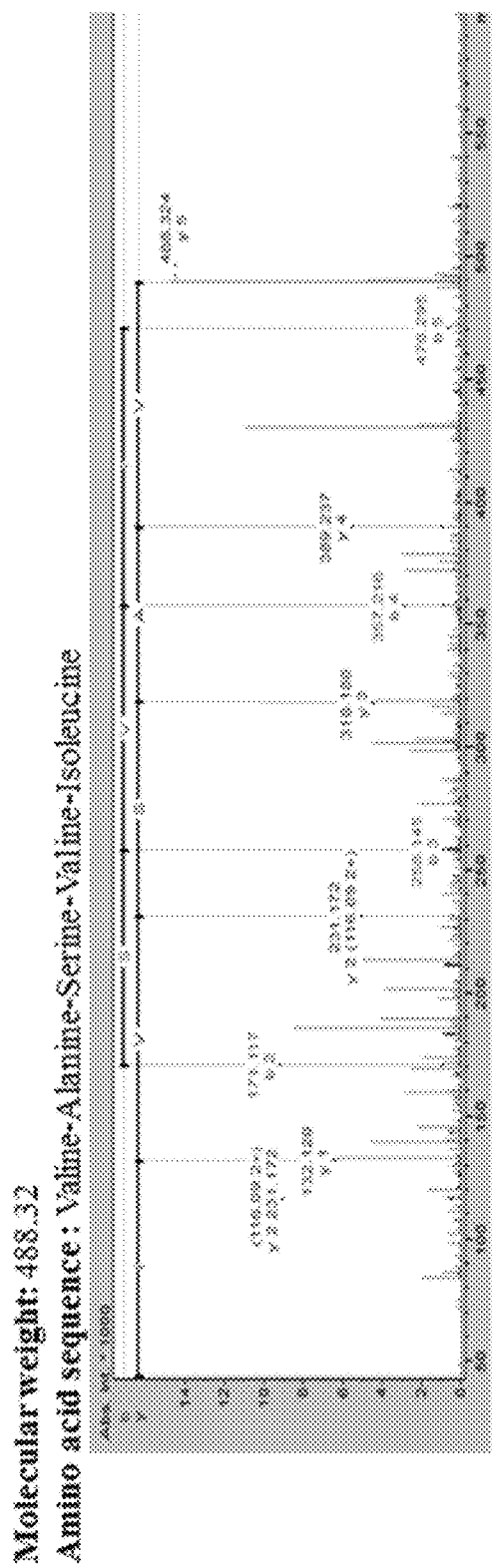
FIG. 9 shows the amino acid sequence, Val-Ala-Ser-Val-Ile (VASVI), of the peptide derived from Fraction 2 and the molecular weight thereof.
Figure 10:
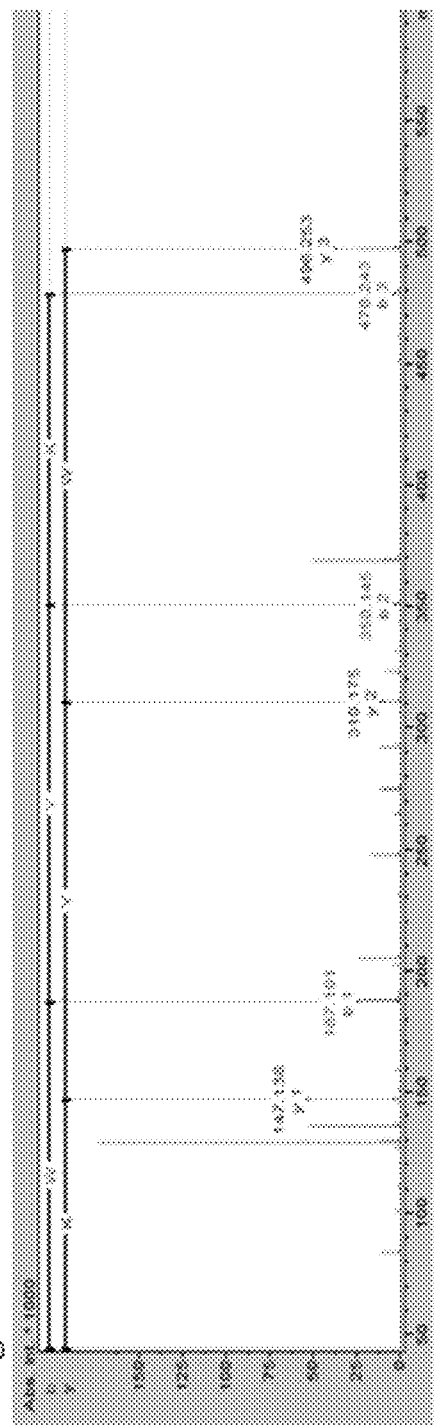
FIG. 10 shows the amino acid sequence, Trp-Tyr-Lys (WYK), of the peptide derived from Fraction 2 and the molecular weight thereof.

Then, the molecular weight and amino acid sequence of the peptides were measured using an electrospray ionization (ESI) Q-TOF mass spectrometer (Micromass, Altrincham, UK) from Fraction F2 that has a high yield and excellent ACE inhibition activity among the fractions. The result is shown in FIGS. 8 to 10. FIGS. 8 to 10 show the amino acid sequence and molecular weight of peptides derived from Fraction 2. As can be seen from FIG. 8, the amino acid sequence of the peptide derived from Fraction 2 was Ile-Val-Asp-Arg (IVDR) (SEQ ID NO: 1), and the molecular weight thereof was 502.30 Da. As can be seen from FIG. 9, the amino acid sequence of the peptide derived from Fraction 2 was Val-Ala-Ser-Val-Ile (VASVI) (SEQ ID NO: 2), and the molecular weight thereof was 488.32 Da. As can be seen from FIG. 10, the amino acid sequence of the peptide derived from fraction 2 was Trp-Tyr-Lys (WYK) (SEQ ID NO: 3), and the molecular weight thereof was 496.25 Da.

TABLE 8

|  | $IC_{50}$ value ACE inhibition activity |
|---|---|
| IVDR (SEQ ID NO: 1) | 32 μg/ml |
| WYK (SEQ ID NO: 2) | 16 μg/ml |
| VASVI (SEQ ID NO: 3) | 57 μg/ml |

The ACE inhibition effect of each of the peptides was also measured. The results are shown as $IC_{50}$ values in Table 8. The IVDR (SEQ ID NO: 1) peptide inhibited 50% of ACE at a concentration of 32 ug/ml, the WYK (SEQ ID NO: 3) peptide showed the lowest $IC_{50}$ value at a concentration of 16 ug/ml, and VASVI (SEQ ID NO: 2) peptide inhibited 50% of ACE at a concentration of 57 ug/ml.

<B. Measurement of Antioxidant Effect>

Example 1: Purchase of Raw Materials and Production of Surimi and Surimi Products The method of producing surimi and surimi products used in the present invention were the same as used in the measurement of anti-hypertensive effect, and the analysis of general components of surimi, heavy metal contents, amino acid composition of flounder, and whiteness and gel strength of surimi also showed the same values as used in the measurement of anti-hypertensive effect.

Example 2: Measurement of Physiological Activity Upon Consumption of Flounder Surimi Product 1) Production of Artificial Digestive Fluids and Treatment Therewith The hydrolysates of the flounder surimi were prepared using an artificial gastric fluid and an artificial intestinal fluid. The same method as used in the measurement of antihypertensive effect was also used for the production of artificial digestive fluids and the treatment with the artificial digestive fluids.

2) Measurement of Radical Scavenging Ability

In order to identify the radical scavenging ability using ESR (electron spin resonance spectrometer, JES-FA ESR, JEOL, Japan), ESR equipment owned by the Center for University-Wide Research Facilities, Jeju University was used and was in accordance with a modified version of the method by Hiramoto (1993). 20 µL of a sample was mixed with 20 µL of distilled water, 20 µL of 40 mM AAPH and 20 µL of 40 mM POBN were added to the resulting mixture, the reaction was proceeded at 37° C. for 30 minutes and the reaction solution was transferred to a capillary tube. The conditions used for analysis were as follows: central field: 3475 G, modulation width: 0.2 mT, 22 amplitude: 500 mT, scan width: 10 mT, set microwave power: 8 mW.

3) Protection Effect of Cells from Oxidative Stress

A monkey kidney fibroblast cell line (Vero, KCKB No. 10081) was used to measure the cell protection effect from oxidative stress. The cells were cultured in an incubator at 37° C. in the presence of 5% $CO_2$. The medium used for culture was Dulbecco's modified Eagle's medium (DMEM, Gibco, USA) supplemented with 10% fetal bovine serum (FBS, Gibco, USA) and streptomycin (100 µL/mL).

4) Morphological Identification of Apoptosis and Necrosis in Cells

In order to morphologically identify apoptosis and necrosis in cells, a slightly modified version of McKeague's method was used. Vero cells were seeded on a 24-well plate at $5 \times 10^4$ cells/well in 500 µL of medium and cultured in an incubator in the presence of 5% $CO_2$ for 16 hours. Then, the cells were treated with a sample on a concentration basis and cultured for 48 hours. The cells were reacted with Hoechst 33342 (1×) and propidium iodide dye for 10 minutes and observed with a fluorescent microscope.

5) Antioxidative Effect in Zebrafish 15 to 20 zebrafish embryos with 7 to 9 hpf (hours post fertilization) were seeded in a 24-well plate and supplemented with 0.9 mL of embryo media. The zebrafish embryos were treated with a sample for 1 hour and then with 50 µL of AAPH, the antioxidant activity was measured through fluorescence (ROS production, lipid peroxidation production, cell death) at 3 dpf (days post fertilization) and viability was measured up to 7 days.

6) Measurement of Reactive Oxygen Species (ROS) in Zebrafish

In order to measure reactive oxygen species (ROS) in the zebrafish, each zebrafish treated with the sample and a stimulator was transferred to a 96-well plate and was reacted with a DCFH-DA solution (20 µg/mL) at 28.5° C. for one hour in a dark area, and the amount of ROS produced was measured. After the reaction, the cells were washed twice with fresh embryo media and then anesthetized with MS-222 (0.003%) for 1 min. The cells were then morphologically observed using a fluorescence microscope and digitized using the image J program.

7) Measurement of Degree of Lipid Peroxidation

In order to measure the degree of lipid peroxidation, each zebrafish treated with the sample and a stimulator was transferred to a 96-well plate and was reacted with a DPPP solution (25 µg/mL) at 28.5° C. for two hours in a dark area, and the degree of lipid peroxidation was measured. After the reaction time, the cells were washed twice with fresh embryo media and then anesthetized with MS-222 (0.003%) for 1 min. The cells were then morphologically observed using a fluorescence microscope and digitized using the image J program.

8) Measurement of Apoptosis in Zebrafish

In order to measure apoptosis in the zebrafish, each zebrafish treated with the sample and a stimulator was transferred to a 96-well plate and was reacted with an acridine orange solution (7 µg/mL) in a dark area at 28.5° C. for 30 minutes and apoptosis was measured. After the reaction time, the cells were washed twice with fresh embryo media and then anesthetized with MS-222 (0.003%) for 1 min. The cells were then observed using a fluorescence microscope and digitized using the image J program.

9) Measurement of Toxicity in Zebrafish

In order to measure toxicity in the zebrafish, 15 to 20 zebrafish embryos with 3 to 4 hpf (hours post fertilization) were injected into each well of a 24-well plate and treated with 50 µL of a sample in the presence of 0.95 mL of embryo media. Heart beating rate was measured at 2 dpf (days post fertilization), toxicity was measured through cell death at 3 dpf and viability was observed up to 7 days.

10) Measurement of Heart Beating Rate in Zebrafish

The measurement of heart beating rate in zebrafish was performed by placing 2 dpf zebrafish on a slide glass and measuring the number of beats of the heart for 1 minute through a microscope.

11) Measurement of Pre-Apoptosis Cytokine in Zebrafish by Real-Time PCR 3 dpf zebrafish were injected into an e-tube and TRIzol reagent was added thereto to induce lysis. The reaction was proceeded for 5 minutes at room temperature, chloroform was added thereto and the reaction was proceeded for 2 to 3 minutes, followed by centrifugation at 12,000 g and 4° C. for 20 minutes to obtain a supernatant. The obtained supernatant was transferred to a fresh e-tube, 100% isopropanol was added thereto, the reaction was proceeded for 10 minutes, the reaction solution was centrifuged at 12,000 g and 4° C. for 10 minutes and the supernatant was discarded. The obtained pellet was washed with 75% ethanol and then centrifuged at 7,500 g and at 4° C. for 5 minutes, the supernatant was discarded and the residue was dried in air for 5 to 10 minutes. RNA was dissolved in 50 mL of RNase-free water at 60° C. for 10-15 minutes. After quantification of RNA, cDNA was synthesized and reacted with produced p53, Bac, Bid, caspase8 and caspase3 amplification primers, and the expression level was identified by real-time PCR.

Figure 11:
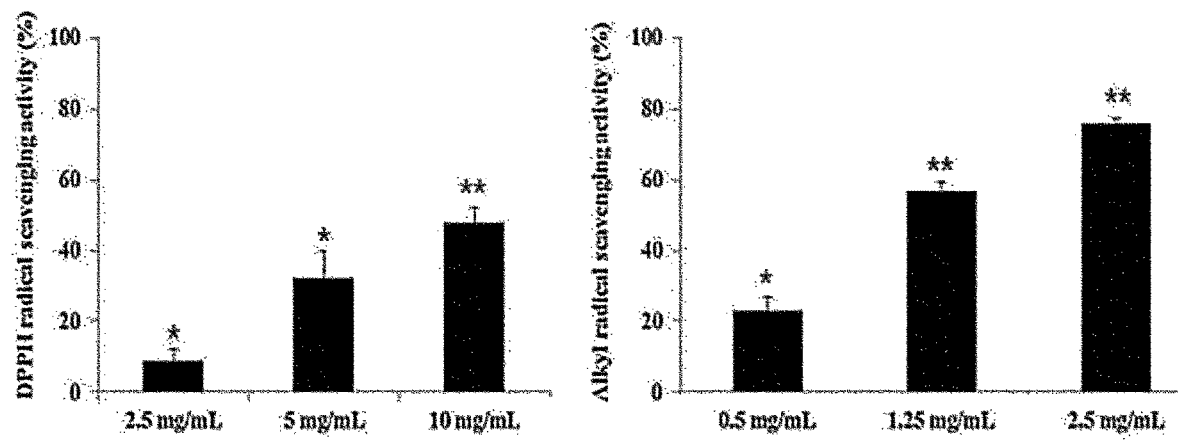
FIG. 11 shows the result of measurement of radical scavenging activity of the flounder surimi hydrolysate.

Experimental Example 1: Measurement of Physiological Activity Upon Consumption of Flounder Surimi A) Measurement of Radical Scavenging Activity of Flounder Surimi Hydrolysate Using ESR Free radicals are well known as a major cause of biological damage. DPPH and alkyl radicals are radicals generally used for the evaluation of antioxidant activity. Therefore, the antioxidant activity of the digested flounder surimi in the body was evaluated, and measurement results of DPPH and alkyl radical scavenging activities are shown in FIG. 11. Substantially, as the concentration increases, the activity tends to increase and the radical scavenging activity significantly increases at each concentration. The DPPH radical scavenging activity was an $IC_{50}$ value of 10.61 mg/mL and the alkyl radical scavenging activity was an $IC_{50}$ value of 1.09 mg/mL.

Figure 12:
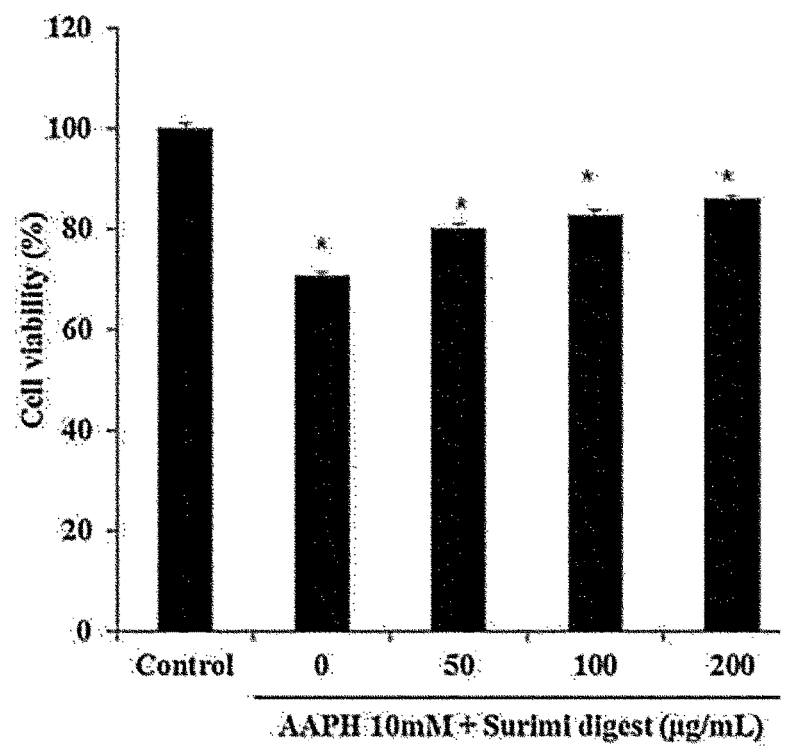
FIG. 12 shows the effect of the flounder surimi hydrolysate on protection of Vero cells from oxidative stress.

B) Oxidative Stress Protection Effect of Flounder Surimi Hydrolysate in Vero Cells Radical scavenging results were obtained using an ESR instrument. Then, oxidative stress was induced in the cells, and how much the flounder surimi hydrolysate protects the cells from ROS was measured using the MTT method. The results are shown in FIG. 12. When the cells were stimulated with only AAPH, cell viability (survival) was 70%, whereas when the cells were treated with the flounder surimi hydrolysate at different concentrations, cell viability (survival) was increased in a concentration-dependent manner.

C) Effect of Flounder Surimi Hydrolysate on Inhibition of Apoptosis

Figure 13:
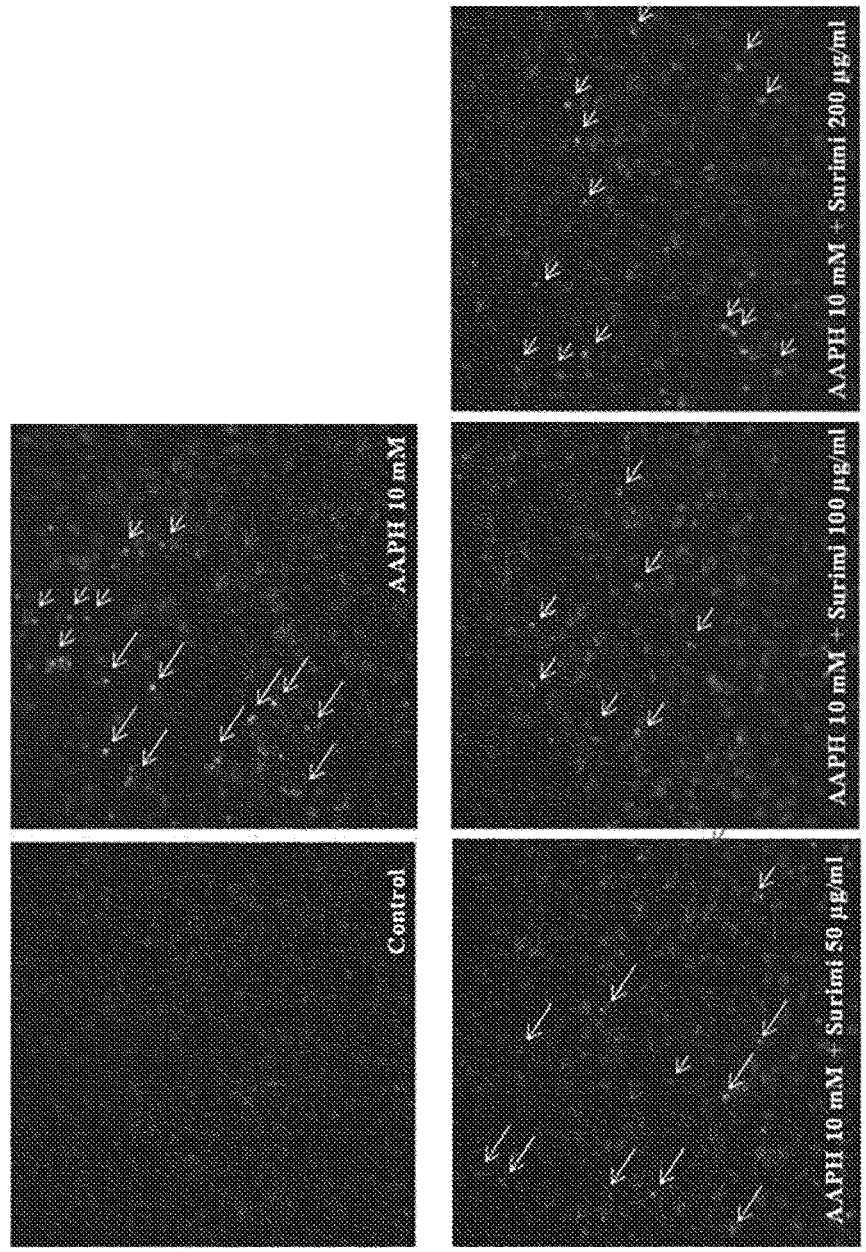
FIG. 13 shows the apoptosis inhibition effect of the flounder surimi hydrolysate.

As the concentration of the sample in Vero cells stained with propidium iodide (PI) and Hoechst 33342 increased, the survival rate of the cells was observed to increase through a microscope. As can be seen from the results of FIG. 13, cells, which were stained white with Hoechst 33342 or were stained red with propidium iodide (PI), were hardly seen in the control group, but apoptosis occurred when AAPH was treated. Thus, it was found that, when the cells undergoing apoptosis induced by oxidative stress were treated with different concentrations of the flounder surimi hydrolysate, apoptosis was reduced in a concentration-dependent manner.

D) Evaluation of Antioxidant Activity in in Vivo Model of Flounder Surimi Hydrolysate Obtained Using Artificial Digestion Enzymes Zebrafish is a model that has been spotlighted as a substitute for mice which are typical experimental animal models. It has a fast life cycle (history) and thus grows to adulthood in six months after hatching from eggs and provides a number of experimental models since it produces about 200 eggs at a time. In addition, it is considerably similar to human organ systems and high genetic homology thereto and is thus commonly used for the research associated with human diseases and functionalities. For the experiment, water temperature was maintained at 28° C., pH was 7.0 to 7.5 and light was emitted for 14 hours a day.

① Measurement of Survival Rate and Heart Beating Rate Using Zebrafish

Figure 14:
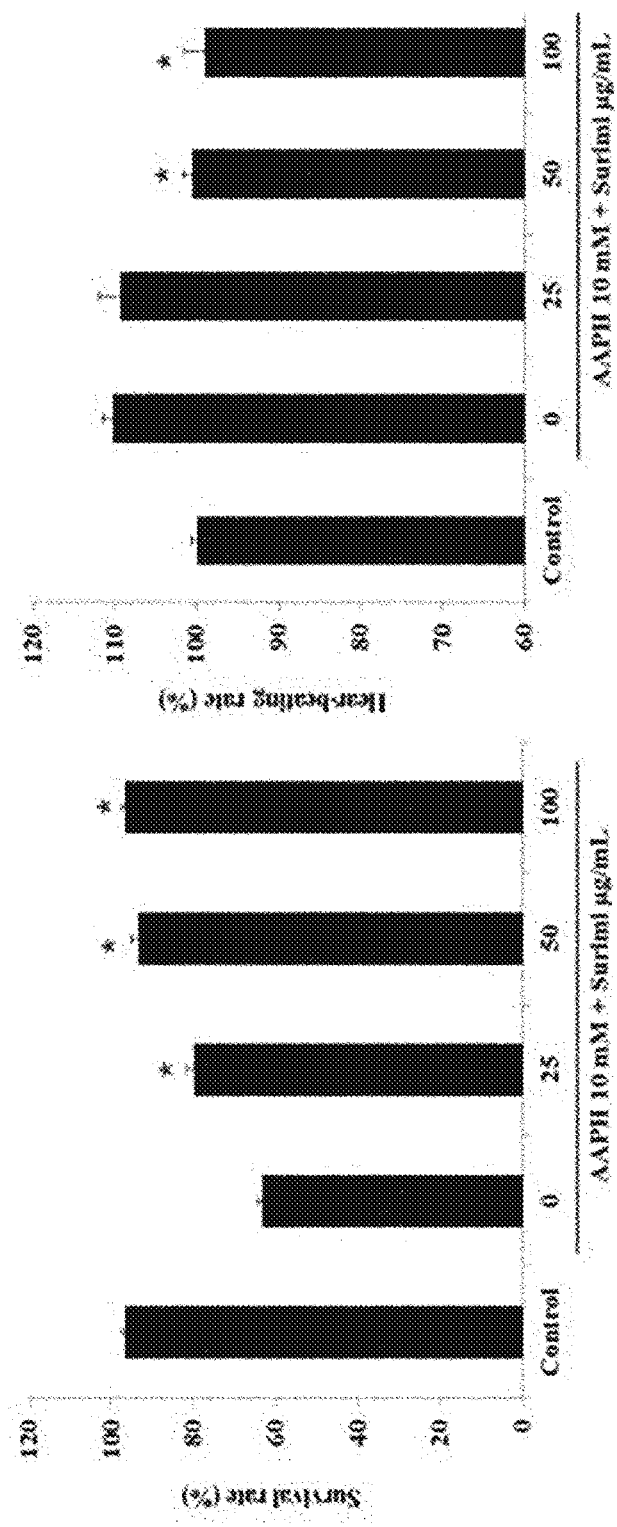
FIG. 14 shows the result of measurement of viability and heart beating rate after treatment of zebrafish with the flounder surimi hydrolysate.

In the present invention, anti-oxidative activity of the flounder surimi hydrolysate were tested in vivo using zebrafish. In zebrafish, AAPH was also used as a stimulant to induce oxidative stress, the survival rate was decreased to 60% after treatment with AAPH for 7 days and the survival rate was increased after treatment with the flounder surimi hydrolysate for 7 days (FIG. 14). It was found that the heart beating rate was also increased by AAPH-induced oxidative stress, whereas the heart beating rate was close to a normal level upon treatment with the flounder treatment hydrolysate.

② Measurement of Inhibition Activity of Flounder Surimi Hydrolysate Against ROS Production How much the flounder surimi hydrolysate decreases ROS production due to oxidative stress was identified. The result (FIG. 15A) showed that treatment with AAPH alone increased ROS production by 30% and the treatment with the flounder surimi hydrolysate decreased ROS production in an concentration-dependent manner. When observed morphologically using a fluorescence microscope, it could be observed with the naked eye that the light emission area formed by ROS production was decreased with treatment with the flounder surimi hydrolysate.

Figure 15:
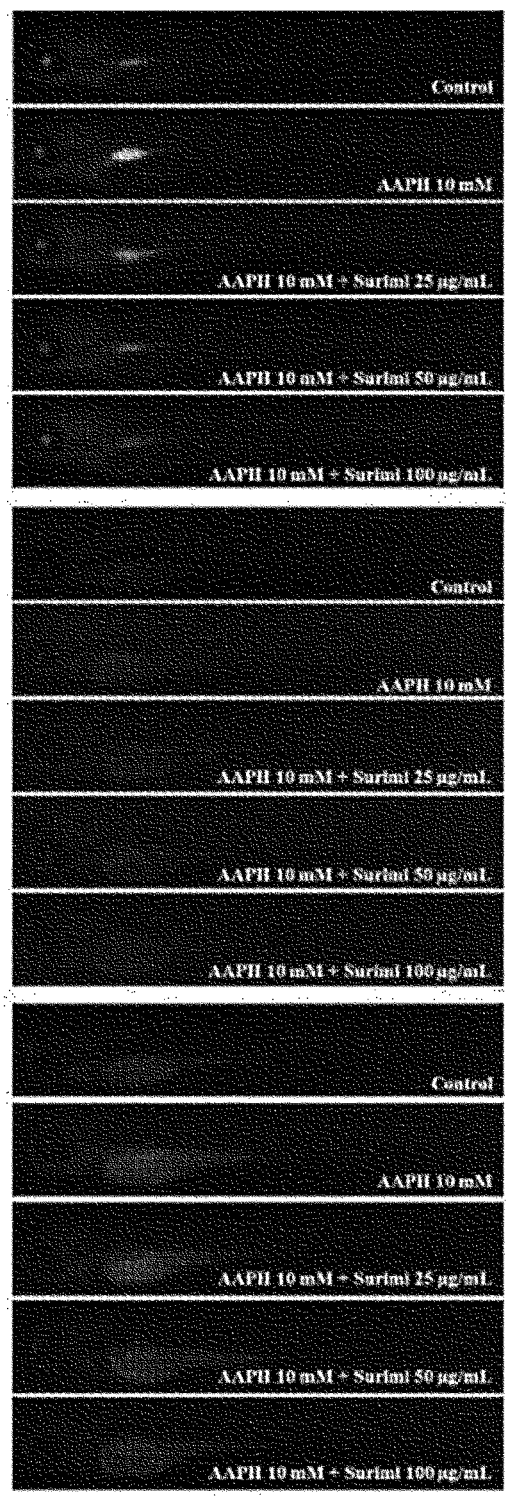
FIG. 15 shows the result of measurement of ROS production, lipid peroxidation and apoptosis after treatment of zebrafish with the flounder surimi hydrolysate fraction.
Figure 15:
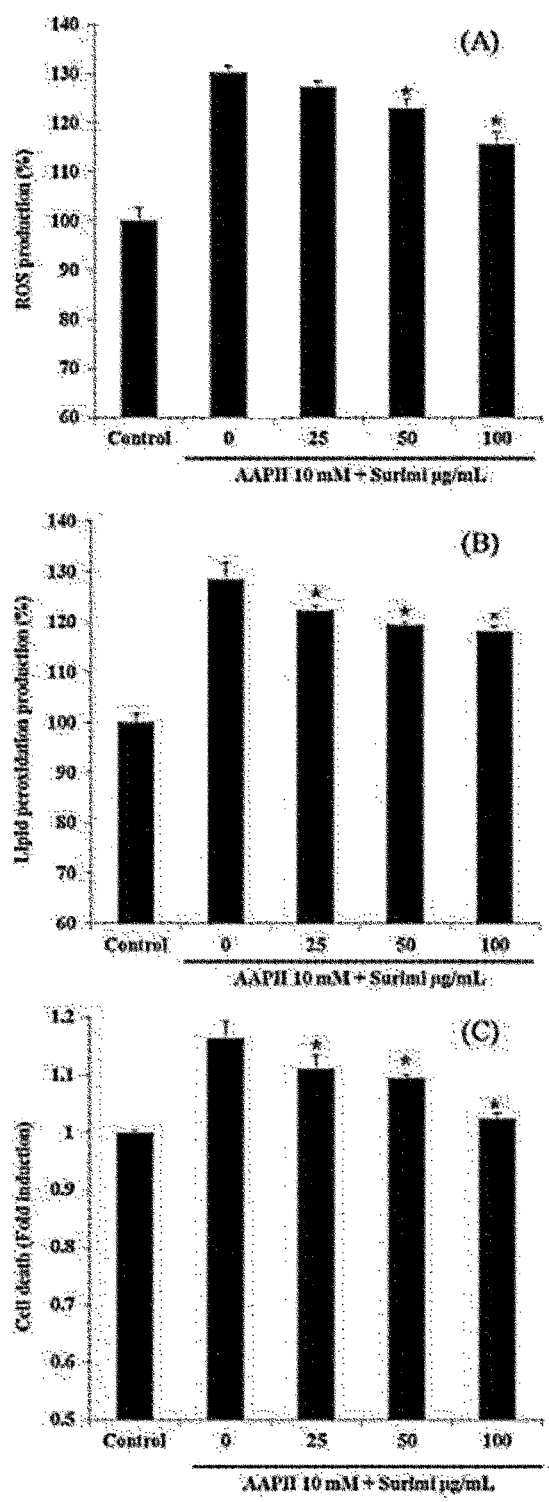

Lipid peroxidation caused by oxidative stress was also decreased depending on the concentration of the flounder surimi hydrolysate (FIG. 15B) and apoptosis was also decreased depending on the concentration thereof (FIG. 15C).

Therefore, the present invention identified based on the in vitro and in vivo experiments that humans have the antioxidant activity when consuming the flounder surimi and actually ingesting the same with digestive fluids through the gastrointestinal tract.

Figure 16:
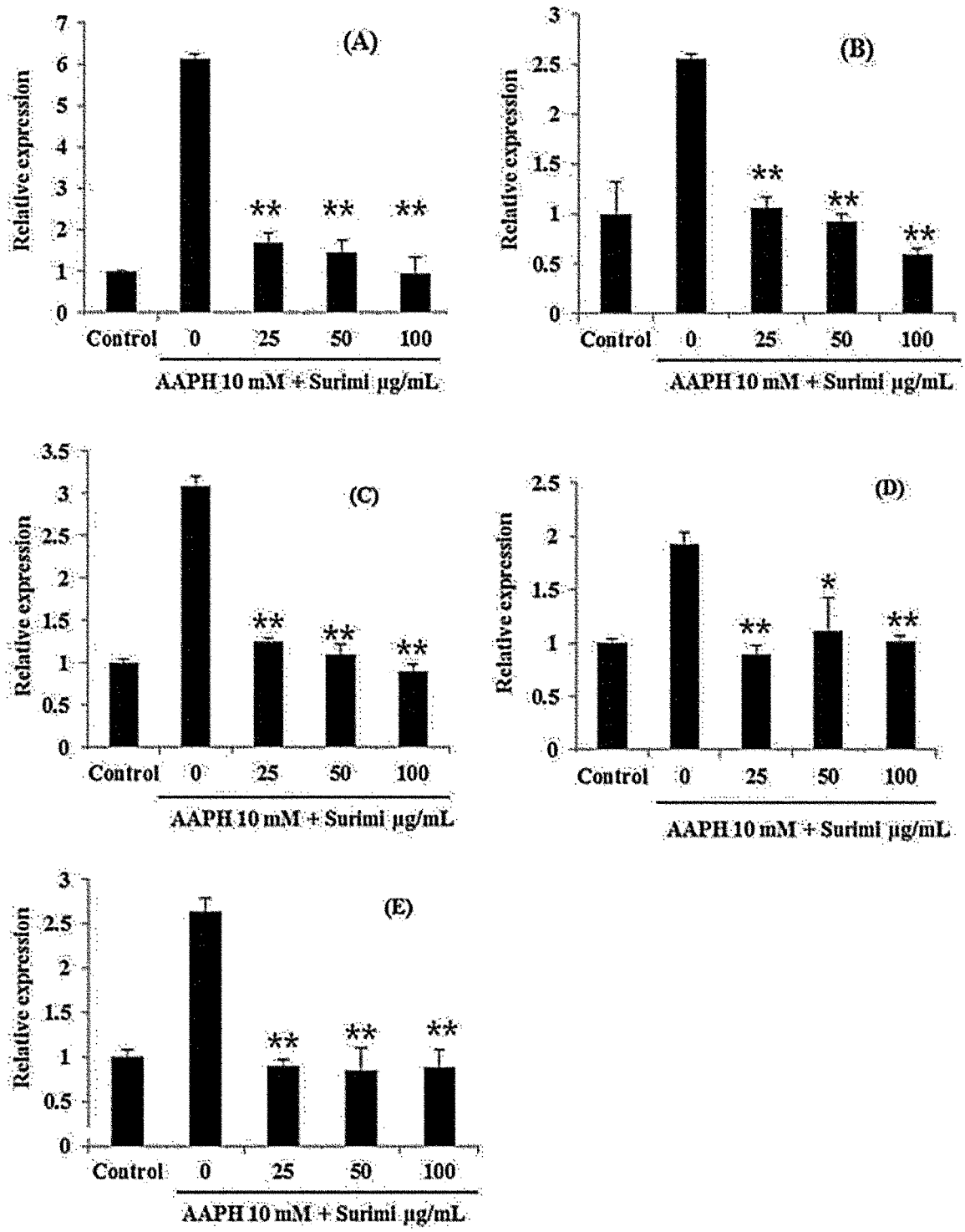
FIG. 16 shows the inhibition effect against Pro-apoptosis mRNA expression upon treatment of zebrafish with the flounder surimi hydrolysate.

③ Inhibition Effect of Flounder Surimi Hydrolysate Against Pro-Apoptosis mRNA Expression When zebrafish were treated with the flounder surimi hydrolysate, whether or not mRNA involved in pro-apoptosis was inhibited was identified. The result is shown in FIG. 16. The major pathway involved in cell apoptosis is known as follows. Damage to cells by external factors results in expression of Bax through p53, which leads to an increase in Caspase 3, 6 and 7, and causes expression of Caspase 8, 10 and Bid. Therefore, cells were treated with different concentrations of the flounder surimi hydrolysate to measure changes in factors involved in cell apoptosis.

It was found that the level was increased in all mRNAs upon treatment with AAPH, which may be expected to induce oxidative stress in zebrafish. In addition, when treated with the flounder surimi hydrolysate samples at different concentrations, p53, Bax and Bid decreased in concentration-dependent manner, and caspase 8 and caspase also did not decrease in a concentration-dependent manner, but the expression thereof was reduced by the flounder surimi hydrolysate.

Figure 17:
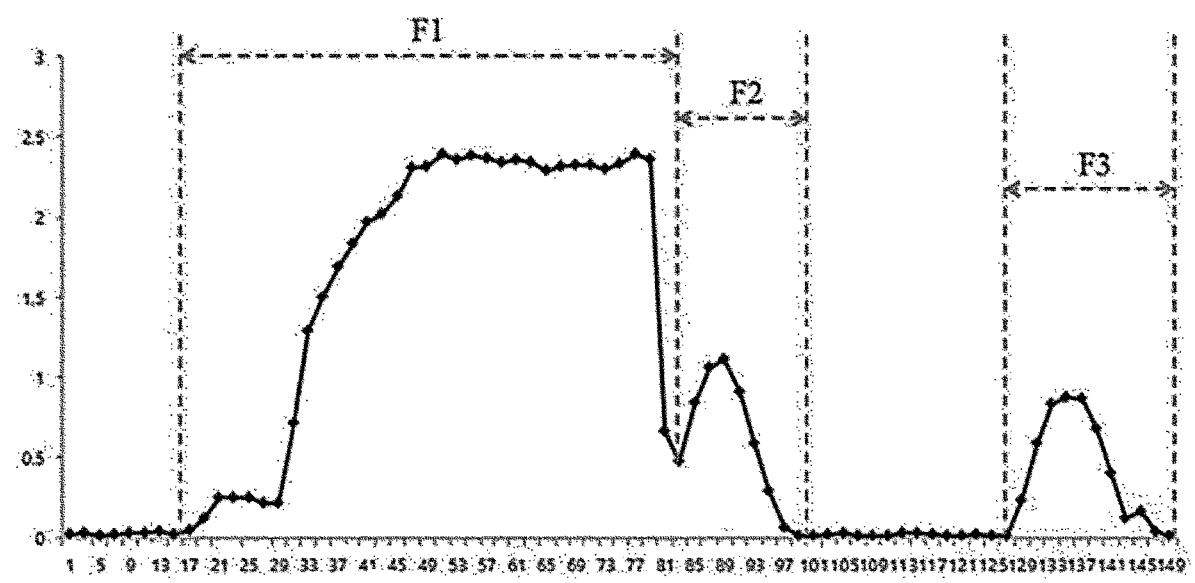
FIG. 17 shows the result of size exclusion chromatography of the flounder surimi hydrolysate using a Sephadex G-25 column.
Figure 18:
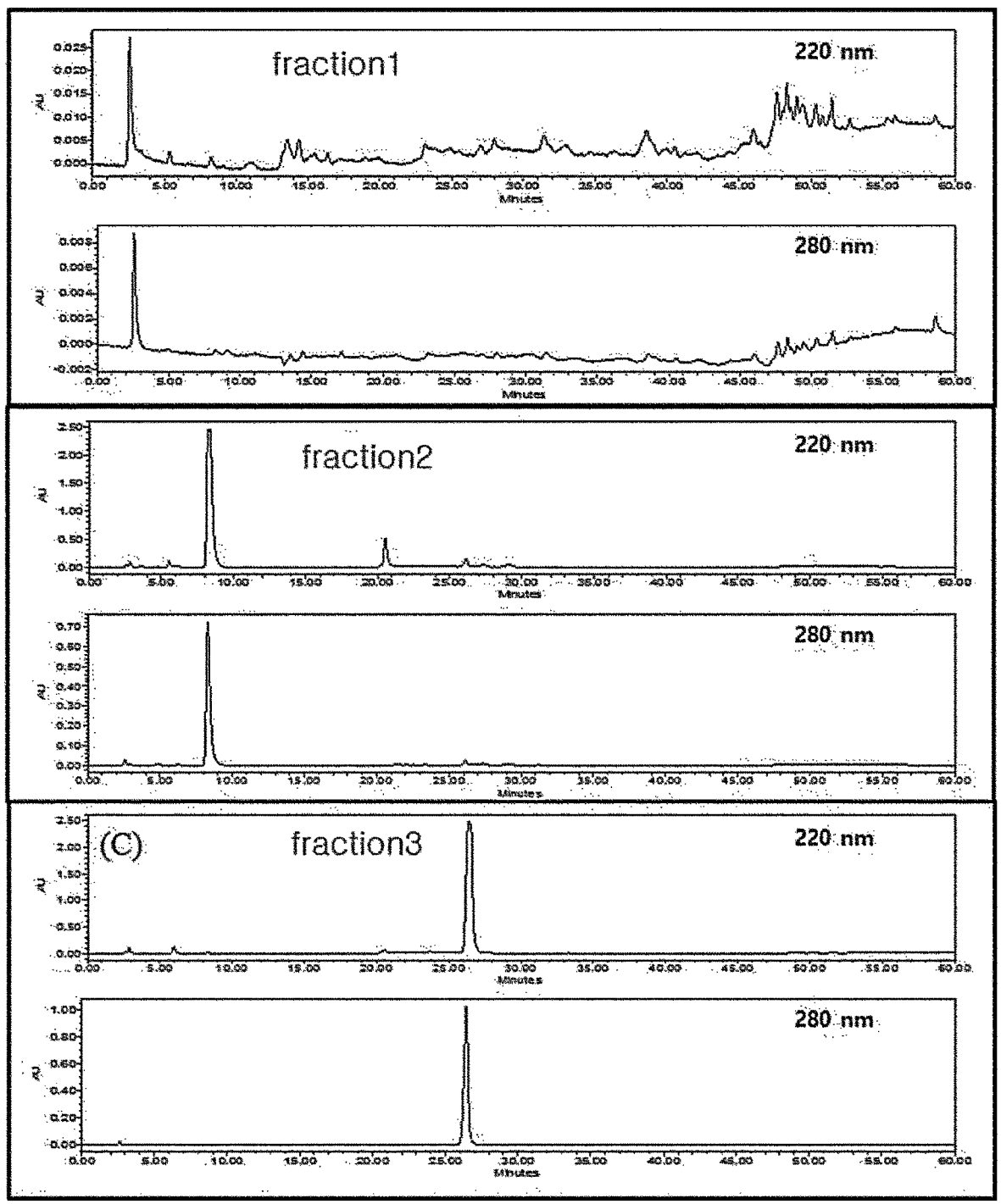
FIG. 18 shows the results of reverse phase chromatograms of flounder surimi hydrolysate fractions.

E) Isolation of Antioxidant Peptides Derived from Flounder Surimi Hydrolysate Using Sephadex G-25 Column A total of three fractions was obtained by fractionizing the flounder surimi hydrolysate on a molecular weight basis using Separdex G-25 and size exclusion chromatography. FIG. 17 shows the result of size exclusion chromatography of the flounder surimi hydrolysate using Separdex G-25. Reverse phase chromatogram of each fraction is shown in FIG. 18 and each fraction was measured at wavelengths of 220 nm and 280 nm. Fraction 1 was considered to contain great amounts of substances since considerably many peaks were detected therefrom. Fraction 2 had a purity of 90% or more since, in addition to one main peak, a small number of peaks were detected therefrom. Fraction 3 had a purity of 95% or more since only one main peak was detected therefrom.

F) Measurement of Alkyl Radical Scavenging Activity of Size-Exclusion Chromatography Fractions The alkyl radical scavenging activity of the three fractions obtained using Sephadex G-25 was measured. As can be seen from Table 9, Fraction 1 contained proteins exceeding 5 kDa, Fraction 2 contained proteins not more than 1 kDa, and Fraction 3 contained proteins less than 1 kDa.

TABLE 9

| | Molecular weight | Alkyl radical scavenging activity (%) |
|---|---|---|
| Fraction 1 | >5 kDa | 31.75% ± 1.88 |
| Fraction 2 | ≤1 kDa | 74.35% ± 0.49 |
| Fraction 3 | <1 kDa | 80.70% ± 0.91 |

Figure 19:
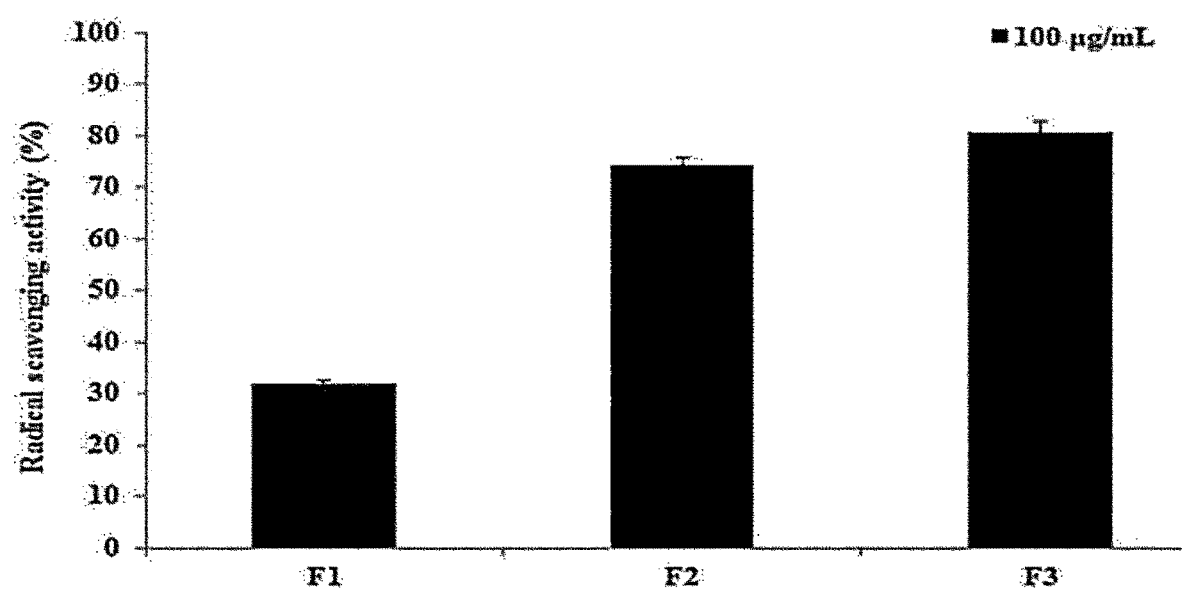
FIG. 19 shows the results of measurement of alkyl radical scavenging activity of the size exclusion chromatography fraction.

FIG. 19 shows the result of measurement of the alkyl radical scavenging activity of the size exclusion chromatography fractions using Sephadex G-25. The result showed that Fractions F2 and F3 showed excellent alkyl radical scavenging activity.

Figure 20:
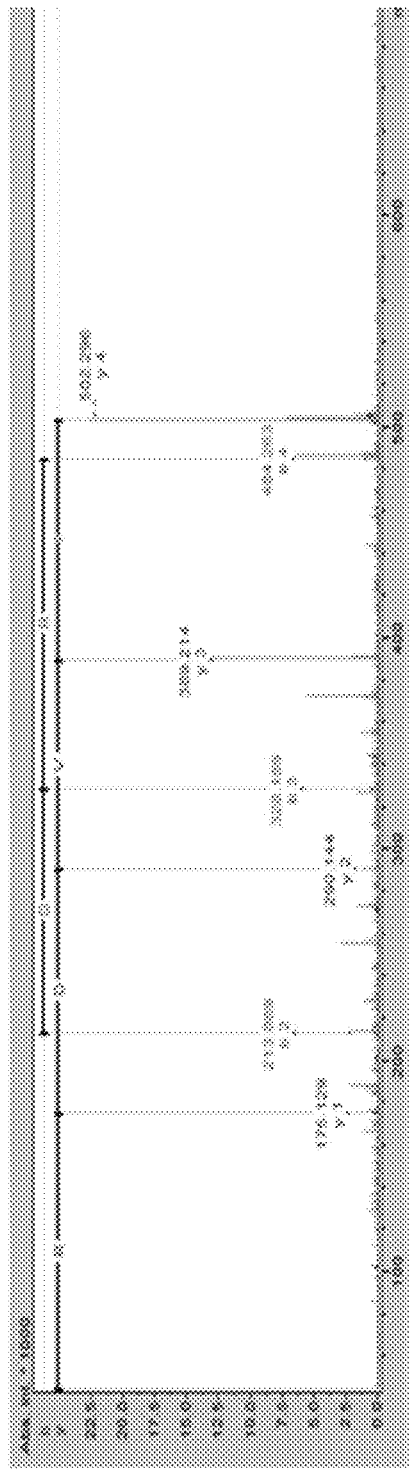
FIG. 20 shows the amino acid sequence, Ile-Val-Asp-Arg (IVDR) (SEQ ID NO: 1), of the peptide derived from Fraction 2 and the molecular weight thereof.
Figure 21:
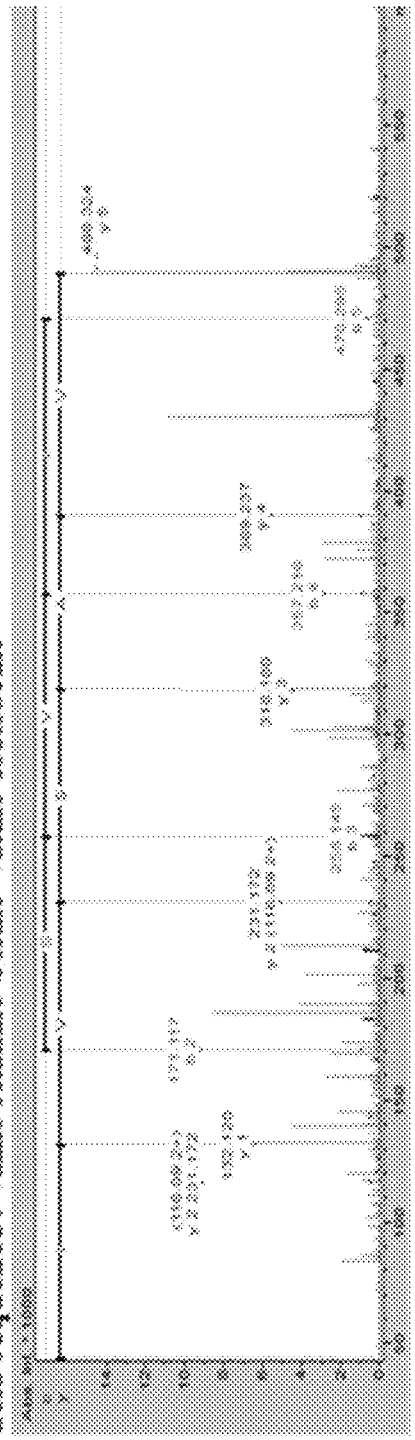
FIG. 21 shows the amino acid sequence, Val-Ala-Ser-Val-Ile (VASVI) SEQ ID NO: 2), of the peptide derived from Fraction 2 and the molecular weight thereof.
Figure 22:
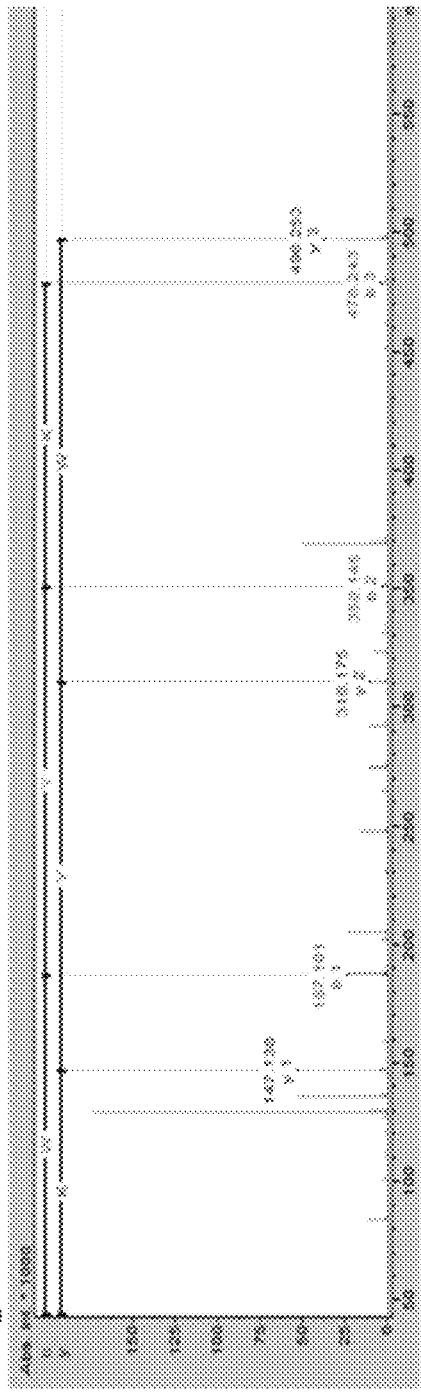
FIG. 22 shows the amino acid sequence, Trp-Tyr-Lys (WYK), of the peptide derived from Fraction 2 and the molecular weight thereof.

Then, the molecular weight and amino acid sequence of the peptides were measured using an electrospray ionization (ESI) Q-TOF mass spectrometer (Micromass, Altrincham, UK) from Fraction F2 that has a high yield and excellent alkyl radical scavenging activity among the fractions. The result is shown in FIGS. 20 to 22. FIGS. 20 to 22 show the amino acid sequence and molecular weight of peptides derived from Fraction 2. As can be seen from FIG. 20, the amino acid sequence of the peptide derived from Fraction 2 was Ile-Val-Asp-Arg (IVDR) (SEQ ID NO: 1) and the molecular weight thereof was 502.30 Da. As can be seen from FIG. 21, the amino acid sequence of the peptide derived from Fraction 2 was Val-Ala-Ser-Val-Ile (VASVI) (SEQ ID NO: 2) and the molecular weight thereof was 488.32 Da. As can be seen from FIG. 22, the amino acid sequence of the peptide derived from fraction 2 was Trp-Tyr-Lys (WYK) (SEQ ID NO: 3), and the molecular weight thereof was 496.25 Da.

TABLE 10

| | $IC_{50}$ value Alkyl radical scavenging activity |
|---|---|
| IVDR (SEQ ID NO: 1) | 68 μg/ml |
| WYK (SEQ ID NO: 2) | 40 μg/ml |
| VASVI (SEQ ID NO: 3) | 77 μg/ml |

Alkyl radical scavenging activity was measured to determine the antioxidant effects of three types of peptides isolated from Fraction 2 of the flounder surimi hydrolysate. The results are shown in Table 10. IVDR (SEQ ID NO: 1) showed 50% radical scavenging activity at the concentration of 68 μg/ml, WYK (SEQ ID NO: 3) peptide showed 50% scavenging activity at a concentration of 40 μg/ml, and VASVI (SEQ ID NO: 2) peptide showed 50% scavenging activity at a concentration of 77 μg/ml.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:
1. A flounder surimi comprising a peptide having an amino acid sequence set forth in SEQ ID NO: 1, SEQ ID NO: 2 or SEQ ID NO: 3 as an active ingredient.
2. A flounder surimi product comprising a mixture of the flounder surimi according to claim 1 and table salt.

* * * * *